(12) United States Patent
Liu et al.

(10) Patent No.: US 7,728,038 B2
(45) Date of Patent: Jun. 1, 2010

(54) METHODS FOR CHELATION THERAPY

(75) Inventors: Gang Liu, Salt Lake City, UT (US); Ping Men, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 155 days.

(21) Appl. No.: 11/197,959

(22) Filed: Aug. 4, 2005

(65) Prior Publication Data

US 2006/0030619 A1  Feb. 9, 2006

Related U.S. Application Data

(60) Provisional application No. 60/599,173, filed on Aug. 4, 2004.

(51) Int. Cl.
*A61K 31/195* (2006.01)
*A61K 31/355* (2006.01)

(52) U.S. Cl. ........................... 514/566; 514/458

(58) Field of Classification Search ............... 514/458, 514/566, 348
See application file for complete search history.

(56) References Cited

U.S. PATENT DOCUMENTS 6,677,320 B2 * 1/2004 Diederich et al. ........... 514/102
6,767,702 B2 * 7/2004 Mirkin et al. ................ 435/6

OTHER PUBLICATIONS

Ima-Nirwana et al., "Palm Vitamin E Improves Bone Metabolism and Survival Rate in Throtoxic Rats", General Pharmacology, Vo. 32, No. 5, pp. 621-626 (May 1999), see enclosed abstract.*
Miller et al., "Duration and Dose-Related Effects of an Orally Administered, Partially Lipophilic Polyaminocarboxylic Acid on the Decorporation of Plutonium and Americium", The Journal of Pharmacology and Experimental Therapeutics, vol. 267, No. 1, pp. 548-554 (1993).*
Chaves et al., "Alkylaryl-amino derivatives of 3-hydroxy-4-pyridinones as aluminium chelating agents with potential clinical application", Journal of Inorganic Biochemistry, vol. 97, No. 1, pp. 161-172 (2003).*

* cited by examiner

*Primary Examiner*—Kevin Weddington
(74) *Attorney, Agent, or Firm*—Ballard Spahr LLP

(57) ABSTRACT

The invention relates to compositions and methods of treatment using an iron chelator, an antioxidant, estrogen, and/or combinations thereof, optionally, linked to a nanoparticle, to treat a subject in need thereof. The compositions and methods may be used to restore or protect the normal functions of osteoblast and osteoclast by depleting iron and inhibiting oxidative damage. The compositions and methods may also be used to increase the bone formation rate in a subject.

14 Claims, 9 Drawing Sheets

2A

Trabecula BMD of spine bone (mg/cm3)

2B

5A

5B

Sham #4  OVX #44  C22 #12

Particle Surface as Backbone

METHODS FOR CHELATION THERAPY

CROSS-REFERENCE TO RELATED APPLICATIONS

This application claims the benefit of U.S. Provisional Patent Application No. 60/599,173, filed Aug. 4, 2004, the entirety of which is incorporated by reference.

STATEMENT REGARDING FEDERALLY SPONSORED RESEARCH OR DEVELOPMENT

This invention was made with government support under Grants 1R21 NS044064-01A1 and 1R03AG21300-01 awarded by the National Institute of Neurological Disorders and Stroke, and the National Institute on Aging. The United States Government has certain rights in the invention.

TECHNICAL FIELD

The invention relates to biotechnology generally and more particularly to compositions containing one or more metal ion chelators and/or chelators conjugated to a nanoparticle and methods of using the same.

BACKGROUND

Iron is an essential nutrient for virtually all cells, including mammalian cells, but iron is a double-edge sword. Iron is an essential element for oxygen transport and numerous biochemical reactions, including oxidation/reduction activity. Excess iron is toxic, causing cellular dysfunction, presumably due to the generation of highly toxic free radicals that can damage all molecular classes found in vivo. Therefore, proper iron regulation is crucial for the health of a subject, including a mammal, such as a human.

Iron produces free radicals, which are highly reactive atoms or groups of atoms that have one or more unpaired electrons. This free radical damage has long been believed to be a risk factor for the degenerative processes that accompany aging in a variety of animal species ranging from insects to humans. These include Alzheimer's and Parkinson's disease, coronary vascular diseases, inflammation and inflammatory disease and other diseases.[1-4] The significant increases are also suggested, albeit controversially, to pose a risk for several chronic diseases, including, heart disease, cancer, diabetes, metabolic disorders associated with insulin resistance syndrome, atherosclerosis, and aging.[5-13]

Because of the long retention time of iron (half life of about 5.5 years), and the lack of a major mechanism of iron excretion in human body, iron accumulation in tissues is a characteristic of aging organisms, despite the fact that some studies show almost no change in the iron concentrations in healthy male livers associated with aging.[14-16] Stored body iron, for example, as estimated by serum ferritin (SF) measurement, increases rapidly after menopause in women and adolescence in men. The increase continues with age and reaches a plateau in about the sixth decade of life. In postmenopausal women, the mean level of storage iron, as reflected by SF concentrations, is 106.3 ng/mL, more than twice that in premenopausal women with 43.0 ng/mL.[17] As will be recognized, postmenopausal osteoporosis is a disease that correlates with the increased mean level of storage iron.

Iron accumulation is also found in adult men, where the mean concentration of serum ferritin (SF) is 121 ng/mL, while males aged from 5 to 19 have a concentration of around 20 to 30 ng/mL.

Therefore, free radical formation may play a role in many diseases. For example, Alzheimer's diseasse, Parkinson's disease, coronary vascular diseases, inflammation and inflammatory disease, heart disease, cancer, diabetes metabolic disorders associated with insulin resistance syndrome, atherosclerosis, and aging.

While the relationship between free radical formation and diseases in skeletal tissues in situ is poorly understood, studies are also beginning to show a connection between free radical damage and skeletal diseases, such as osteoporosis. For instance, a mitochrondrial DNA deletion has been associated with systemic oxidative stress and severe osteoporosis in human males.[18] Furthermore, antioxidant administration (e.g., vitamin E or citrus flavonoid) increases the bone mass of animals.[19,20]

With the widespread and diverse implications for iron accumulation in vivo, there is a need in the art for treatments that may reduce, prevent or treat disease commonly associated with increased iron concentrations. Two examples of such diseases are osteoporosis and Alzheimer's disease.

Postmenopausal osteoporosis is a disease in which bones lose strength leading to an increased risk of fracture. One in two women over age 50 will have an osteoporosis-related fracture during their lives. Moreover, in the United States there are millions of women who have osteopenia, placing them at increased risk for postmenopausal osteoporosis. This disease has presented a big health problem not only for the United States, but also worldwide because approximately 200 million women suffer from this disease and it is increasing in significance as the population of the world both grows and ages. Also, postmenopausal osteoporosis and associated fractures put a heavy economic burden on society because of disability, decreased quality of life, and mortality. According to the International Osteoporosis Foundation, annual direct medical costs to treat 2.3 million osteoporosis fractures in Europe and in the United States of America are about $27 billion.

Furthermore, the lifetime risk of dying from osteoporotic hip fractures alone (about 20% of all osteoporotic fractures (NIH)) is the same as that of dying from breast cancer, and the risk of osteoporosis is greater than breast, cervical and endometrial cancer combined.

Alzheimer's disease (AD) is a progressive, degenerative, and irreversible brain disorder that is ultimately fatal. It is the most common form of dementia among people age 65 and older.[21] Currently, about 4 million Americans suffer with the disease and approximately 360,000 new cases will occur each year. AD presents a big health problem, not only for the USA, but also worldwide, because of its enormous impact on individuals, families, the health care system, and society as a whole. The annual national cost of caring for AD patients has been estimated to be over $100 billion. Unfortunately, there is no known cure for AD at the present time.

Presently only acetylcholinesterase inhibiting drugs are approved by the Food and Drug Administration for treatment of AD in the US; they are Aricept (donepezil), Cognex (tacrine), Rivastigmine (Exelon), and Galantamine (Reminyl, also acting as an allosterically potentiating ligand on nicotinic acetylcholine receptors).[21-23] Although treatment with these drugs provides symptomatic improvements or delays in the progression of cognitive, behavioral, and functional deficits, it does not stop or reverse the progression of AD.

Other methods of treatment that have received some attention include anti-inflammatory drugs[18], antioxidants[24], estrogen, and nerve growth factor.[21] Therefore, there remains a strong need in the art for additional treatment methods.

Accumulating evidence supports the hypothesis that oxidative stress generated by various mechanisms may be among the major intermediary risk factors that initiate and promote neurodegeneration in AD.[25-28] Many reports show that the metabolism of iron is involved in AD and that the concentration of iron in the brain of AD patients is elevated.[29] Smith et al. studied the distribution of iron in the brain of AD patients using various histochemical methods and observed that the iron distribution matched the distribution of senile plaques (SP) and neurofibrillary tangles (NFT), the two hallmark pathologies of AD.[8,10] Aluminum (Al) has also been shown to accumulate in the central nervous system and modulate the formation and deposition of A$\beta$ in the brain [161]. Al, unlike transition metal ions, is unable to redox cycle in electron transfer reactions due to a fixed oxidation state of $3^+$ in biological systems, but growing evidence suggests that it can act synergistically with iron to increase free radical damage.[30] Strong evidence also shows that other metals are implicated in the development of AD, including, but not limited to, copper and zinc.[31-38]

Overall, these studies indicate that the environment in the brain in AD, due to imbalances of several metal elements has the potential of catalyzing and stimulating free radical formation and enhancing neuron degeneration.

The elevated concentration of so many metals has previously looked too complex to be dealt with. However, the invention provides a unique opportunity for chelation therapy for the treatment of numerous diseases, including, but not limited to, AD and osteoporosis.

SUMMARY OF THE INVENTION

The invention relates to compositions and methods of treatment using an iron chelator, an antioxidant, estrogen, and/or combinations thereof to treat a subject in need thereof. The compositions and/or methods of the invention are useful in the treatment of any disease caused by, or exacerbated by, a metal ion. In an exemplary embodiment, the compositions and/or methods of the invention are used to restore or protect the normal functions of osteoblast and osteoclast by depleting iron and inhibiting oxidative damage. In another exemplary embodiment, the compositions and/or methods of the invention are used to increase the bone formation rate in a subject. In yet another exemplary embodiment, the compositions and/or methods of the invention are used to treat Alzheimer's Disease. In yet another exemplary embodiment, the compositions and/or methods of the invention are used to treat neurodegenerative diseases, such as Parkinson's disease and Friedreich's ataxia. In a further exemplary embodiment, the compositions and/or methods of the invention are used to treat iron overload.

In another exemplary embodiment, iron chelator nanoparticles are used to target desired organs of a subject in iron chelation therapy.

In another exemplary embodiment, iron chelator nanoparticle comprises bidentate, tridentate and/or hexadentate iron chelators conjugated to a nanoparticle. In yet another exemplary embodiment, the iron chelator nanoparticle is used to remove iron and other metals from the brain of a subject.

In another embodiment, the chelator-nanoparticle system is chelated with a non-radioactive and/or radioactive metal ion and, optionally, is used to target a diseased tissue or organ for diagnosis and/or treatment.

In another embodiment, the chelator-nanoparticle system is used for disease diagnostic imaging.

In another exemplary embodiment, the invention comprises a medicament and a method of producing a pharmaceutical medicament for the treatment of a disease produced, or exacerbated, by a free metal ion.

DETAILED DESCRIPTION OF THE INVENTION

Figure 1:
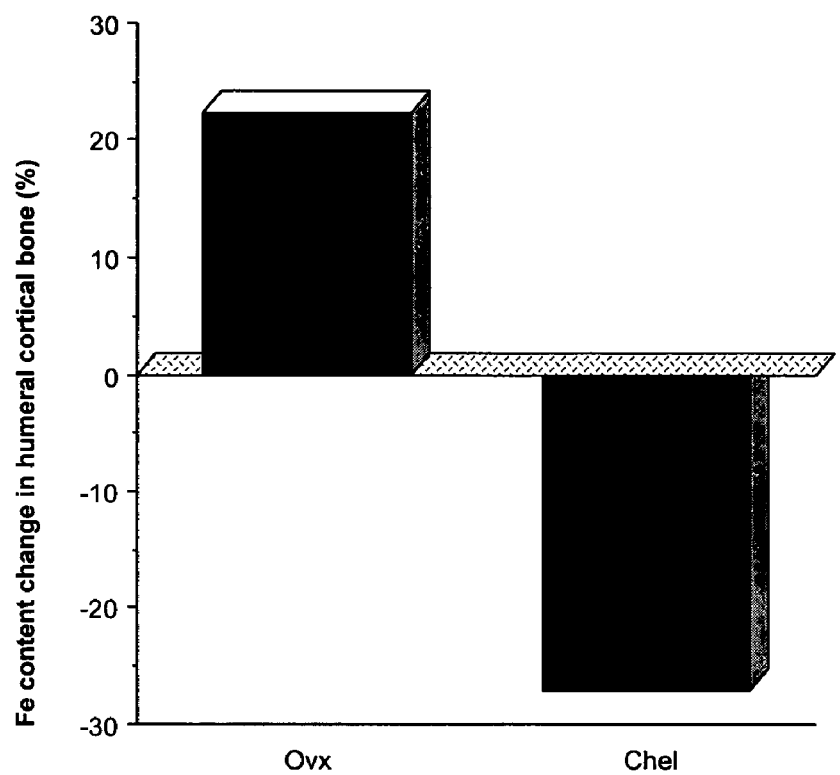
FIG. 1. Illustrates the percentage of free iron contents in Ovx rat bone (Ovx) and chelator treated Ovx rat bone (Chel) compared with Sham controls, respectively. The free iron contents are significantly different between the groups of Ovx, Chel and Sham ($p<0.01$ by ANOVA. $n=6$ per group).

The present invention demonstrates that iron chelation therapy is beneficial in the reduction of iron and, as such, provides a therapeutic approach to diseases influenced by increased metal content. For example, deposits of excess iron in the bone of patients with primary or secondary iron-overload plays a pathologic role in skeletal diseases. Hence, the present invention provides a therapeutic approach to these diseases.

The present invention confirms that iron concentrations increase in osteoporotic and osteopenic bone of postmenopausal women and estrogen deficient animals, respectively. Most importantly, it is shown, for the first time, that iron reduction in bone by chelation therapy mitigates the development of osteopenia in estrogen deficient rats. Thus, indicating a causative role of iron in postmenopausal osteoporosis and providing a therapeutic strategy for treatment or prevention of the disease.

In another exemplary embodiment, the invention provides compositions and/or methods for the treatment of AD, for example, a high affinity iron chelator may be used to treat or prevent the disease. Optionally, the chelator may also have an affinity for Al, Cu, and Zn. Metal chelation may be a reason why Desferrioxamine (DFO), a specific iron chelator with high affinities for Al, Cu, and Zn, has some therapeutic benefits for patients with AD.

As used herein, "treating" or "treatment" does not require a complete cure. It means that the symptoms of the underlying disease are at least reduced or delayed, and/or that one or more of the underlying cellular, physiological, or biochemical causes or mechanisms causing the symptoms are reduced, eliminated and/or delayed. It is understood that reduced and/or delayed, as used in this context, means relative to the state of the disease or the expected state of the disease, including the molecular state of the disease, not just the physiological state of the disease.

As used herein and in the appended claims, the singular forms, for example, "a", "an", and "the," include the plural, unless the context clearly dictates otherwise. For example, reference to "a chelator" includes a plurality of such chelators, and reference to a "long-live organic free radical" is a reference to a plurality of similar long-live organic free radicals, and equivalents thereof.

To demonstrate the utility of chelation therapy in the treatment of osteoporosis, the present invention shows that in osteoporotic bone induced by estrogen deficiency, the contents of both iron and long-live organic free radicals (LLOFR, oxidized organic compounds that can serve as biomarkers of oxidative damage) increase compared with age-matched controls. More specificly, using Electron Paramagnetic Resonance (EPR) techniques (see, U.S. Pat. Nos. 4,888,554; 6,573,720; 5,781,011; 5,678,548; 5,327,084; 5,159,269; 5,149,946; and 5,030,914), it has been found that the levels of free iron (non-protein-bound iron, which is highly active in catalyzing free radical formation) are elevated in osteoporotic and osteopenic bone of postmenopausal women and ovariectomized rats, respectively, compared with controls. Without wishing to be bound by theory, it is hypothesized that the direct accumulation of iron in bone of postmenopausal women increases the risk of developing osteoporosis.

Heavy metal excretion from rats treated by GL22: In addition to iron removal from bone, the chelator GL22 also has the ability to remove other heavy metals (for example, Americium and Plutonium) from bone and, most importantly, deplete Fe, Pu and Am from the body. It is desriable for chelation therapy to remove excess metals from the diseased tissues, to avoid redistribution of these metals inside the body. Indeed, GL22 chelator was used to treat heavy metal overload animals, without any indications of toxicity.[39,40]

In another exemplary embodiment, a chelator that can increase the Ca bioavailability by chelating Ca and delivering the element to bone is used to prevent bone loss.[41] This embodiment may be tested by examining the distribution of radioactive isotopic Ca in OVX rats treated with chelator. Copper is another essential trace metal that is also harmful in excess, due to catalyzing formation of free radicals. In another exemplary embodiment, a chelator, e.g., GL22, having a high binding affinity for Cu (GL22=$10^{17}$) to remove Cu from bone and assist in the bone protective mechanism of chelator therapy.[40-42] The copper content in bone may be measured by, for example, using chelator treated OVX rats. A decrease in the Cu content of chelator treated OVX rats, compared with OVX controls, indicating that Cu may be involve in bone loss of OVX rats.

The chelator of the invention may be used in mammals, for example, animals, such as horses, cows dogs, cats, porcine, primates or humans, particularly, as a therapeutic for postmenopausal osteoporosis or AD.

In another exemplary embodiment, the invention provides a chelator coupled to a nanoparticle. The term nanoparticle appears in medical literature quite often. In most cases it is used to describe objects of from about 30 to about 300 nm in diameter represented by vesicles, polymers or colloids. These species are used for drug delivery and for diagnostic purposes. In addition, nanoparticles (NPs) may combine properties of bulk solids and relatively large molecules. The core of NPs may be made of inorganic material and retains some physical and chemical properties of its bulk predecessor, while the solubility and chemical reactivity is determined by a thin, virtually monomolecular layer, of organic molecules adsorbed to the NP. This layer passivates the surface of the solid and protects the NP from further growth. A chemical compound forming this layer is often referred to as a stabilizer. The inorganic core may contain 100 to 10,000 atoms depending on its diameter (1-10 nm). The size may be accurately assessed by the position of UV absorption peak that was shown to shift to shorter wavelengths for smaller NPs due to size-quantization effect. Nanosparticles, as well as carrier particles, may be made of a polymer material, i.e., polystyrene. However, polymeric materials including, but not limited to, brominated polystyrene, polyacrylic acid, polyacrylonitrile, polyamide, polyacrylamide, polyacrolein, polybutadiene, polycaprolactone, polycarbonate, polyester, polyethylene, polyethylene terephthalate, polydimethylsiloxane, polyisoprene, polyurethane, polyvinylacetate, polyvinylchloride, polyvinylpyridine, polyvinylbenzylchloride, polyvinyltoluene, polyvinylidene chloride, polydivinylbenzene, polymethylmethacrylate, polylactide, polyglycolide, poly (lactide-co-glycolide), polyanhydride, polyorthoester, polyphosphazene, polyphosophaze, polysulfone, or combinations thereof are acceptable as well. Other polymer materials such as carbohydrate, e.g., carboxymethyl cellulose, hydroxyethyl cellulose, agar, gel, proteinaceous polymer, polypeptide, eukaryotic and prokaryotic cells, viruses, lipid, metal, resin, latex, rubber, silicone, e.g., polydimethyldiphenyl siloxane, glass, ceramic, charcoal, kaolinite, bentonite, and the like may also be used.

In connection with the present invention, the nanoparticle may be covalently linked to other molecules, such as an antibody, antibody fragment, peptide, hormone, lipid or others. Such other molecules may be used to increase the targeting of the chelator nanoparticle system to a particular organ or cell type.

The linker between the nanoparticle and the chelators is selected from the group consisting of a hydrogen, and/or a straight or branced, substituted or unsubstituted, alky, aryl, alkene, alkyne, hydrogen, and/or alkylaryl, in such a way that it is far enough removed from the surface of the nanoparticle to be biologically active, reduce steric hindrance, and increase activity. Another method that may be used is to first adsorb a carrier molecule with available surface functional groups, such as bovine serum albumin or polylysine, and then covalently attach the chelators to surface functional groups on these carrier molecules. In addition, the design and synthesis of more biocompatible polymeric nanoparticles with optimally functional linkers for chemically bonding iron chelators is performed. More importantly, all of these approaches may be used to optimize the particle surface properties, hence increase the targeting and penetration abilities, using the guidance of the specification. The invention further provides for the conjugation of the iron chelators to nanoparticles with chemical bonds that are more stable than amido bond, for example, carbon-carbon bonds to avoid the possible break of the amido bond under the biological environment in human. The concentration of chelator conjugated to a nanoparticle may be varied, particularly to influence the system surface properties and chelating efficiency.

Additional descriptions of linker molecules, nanoparticle compositions and the like may be found in U.S. Pat. Nos. 6,767,702; 6,689,338; 6,653,519; and 6,649,414.

The chelators of the invention optionally, exclude citrate, EDTA, ferritin and/or deferoxamine.

Prior to the present invention, there have been no reports that synthetic hexadentate iron chelators can pass the BBB due to their hydrophilicity and relatively large molecular weight.[43] Although there are some promising studies on nanoparticulate systems to deliver drugs to the brain, these reports do not demonstrate that nanoparticulate systems can deliver iron chelators to specific organs and/or remove iron-chelator complexes from sites of excess metal accumulation.

DFO was found to significantly slow the progression of AD in one clinical trial.[47] In this study, the chelation of Al was examined, but it is possible that the therapeutic effect may also have been due to removal of Fe since DFO preferably chelates iron.[48,49] DFO also has an appreciable affinity for Cu and Zn.[48,50] The affinity constants of DFO for Fe(III), Al(III), Cu(II), and Zn(II) are 30.6, 22, 14.1, and 11.1 (logK/M), respectively.[51] In the clinical study (above), Cu and Zn, unfortunately, were not monitored. Therefore, it is not clear if the possible removal of Cu and Zn by DFO treatment also played a role in slowing the clinical progression of AD. However, some studies have implied that chelators which chelate Cu and Zn have the ability to dissolve Aβ amyloid plaques which deposits in AD.[52-53]

DFO is the only chelation drug approved by the FDA for iron overload. DFO therapy promotes iron excretion and has led to great improvements in the quality and duration of life of patients who suffer from β-thalasemia and other refractory anemias. In addition, DFO also inhibits nigrostriatal degeneration induced by 6-hydroxydopamine. Unfortunately, DFO has serious side effects including neurotoxicity and neurological changes. Furthermore, DFO is poorly absorbed by the gastrointestinal tract and rapidly degrades after administration. Therefore, it requires long subcutaneous administration to effect significant iron excretion. Moreover, DFO does not easily penetrate the BBB due to its hydrophilic nature.[54-55] Some penetration may occur due to the compromise in the BBB at the lesion sites.[54] All these drawbacks make it very difficult to use DFO for the treatment of AD. Conjugation of DFO to a nanoparticle may be used to overcome or reduce these drawbacks.

Deferiprone or L1 (1,2-dimethyl-3-hydroxyl-4-pyridinone) is an iron and aluminum chelator approved in Europe, but not the United States. Although L1 has high oral activity and BBB penetration ability due to its lipophilicity, its use has been limited because of serious side effects. In addition, studies have shown that L1 lacks the ability to remove iron from the brain probably due to strong hydrophilicity of the iron-L1 complex. Additional, there is no carrier-mediated transport system available to remove the complex from the brain. Other L1 derivatives with higher lipophilicity also have the ability to cross the BBB and complex brain iron, but they also possess considerable neurotoxicity.[56-57]

Thus, the use of the currently available iron chelators are limited by their poor transfer across (both ways) the BBB and their toxicity. Most bi- or tridentate iron chelators with small molecular weight and high lipophilicity have the ability to penetrate BBB, but show toxicity.[51] Hexadentate iron chelators are considered better candidates for chelation therapy than bi- and tridentate ones because of their lower toxicity before and after chelation.[51] However, they have difficulty penetrating the BBB due to their hydrophilicity and relative high molecular weight. One strategy to increase the BBB penetration is by enhancing the lipophilicity and lowering the molecular weight of the iron chelators, but this is believed to increase toxicity.[64] In addition, it is possible that many lipophilic drugs which normally should cross the brain endothelial cells are rapidly pumped back into the blood stream by extremely effective efflux pumps[61], which include multiple organic anion transporter and P-glycoprotein (multidrug resistance protein). Many promising attempts have been made to develop iron chelators with oral activity (membrane penetration) and low toxicity for the treatment of iron overload disease.[65-70]

Some existing USP drugs that possess chelation properties and BBB penetration ability may have therapeutic benefits in AD. But these drugs generally may have a low affinity for iron and would be toxic at doses needed for chelation therapy. Other therapeutic approaches are being explored to overcome the impediment of the BBB. For example, a prochelator has been designed for the purpose of entering the BBB. The functional groups of the prochelator are activated by enzymatic or non-enzymatic reactions only after they have entered the target organ. Another example is to use simple inorganic silicate, which can form very stable complexes with many metals and probably has the ability to enter the BBB. Iron chelators designed with near-optimal lipophilic/hydrophilic balance of the free chelator and iron complex for the purpose of passage into and out of the cell have been synthesized and studied. However, the lipophilic/hydrophilic balance may change upon binding to a metal, thereby making the design of such a balanced chelator extremely difficult.

Nanoparticles made of natural or artificial polymers ranging in size from about 10 to about 1000 nm present a useful tool to transport drugs across the BBB. The advantages of nanoparticles include reduced drug toxicity, improved biodistribution and therapeutic efficacy. The particles are believed to mimic low density lipoprotein (LDL) and interact with the LDL receptor, resulting in their uptake by brain endothelial cells. The transferrin transcytosis systems may also be employed by the particulated drug delivery system to deliver drugs into the brain. The invention provides an iron chelator covalently attached to a nanoparticle, wherein the particle may serve as a targeting vehicle to deliver the chelator to the brain, for example, by facilitating passage across the BBB.

There are three advantages to invention: first, the chelators need not be lipophilic to cross the BBB; second, the lipophilic character of the chelator no longer contributes to potential toxicity; and third, hydrophilic hexadentate iron chelators with large molecular weights may be used.

In a preferred embodiment, the chelator nanoparticle must be capable of leaving the brain with the metal complex. In this embodiment it is preferable that the nanoparticle is not biodegradable, thus, the same carrier-mediated transport systems are able to carry the iron complex particles in and out of the brain. In contrast, lipophilic chelators can enter the brain, but when complexed with metals are unable to cross the BBB due to a change in their lipophilicity. For example, the distribution coefficient (DC) of free L1 determined in n-octanol/

Tri-HCl buffer system is 0.24, but the DC of the iron bound L1 complex drops to 0.0009.[71] Indeed, although L1 can reportedly penetrate the BBB, it fails to remove iron from the brain. In addition, the increase in lipophilicity will decrease the solubility in aqueous solution which may decrease the bioavailability. Conjugation of the iron chelator with a nanoparticle is believed to permit the chelator and the chelator-metal complex (which allows the use of even larger hydrophilic hexadentate chelators) to cross the BBB and decreases toxicity.

The invention provides synthesized bidentate, tridentate and/or hexadentate iron chelators, which may be conjugated to nanoparticles to produce chelator nanoparticles. These chelator nanoparticles are believed to target the brain, remove iron from the brain, and/or protect from iron-induced oxidative damage in the brain of a subject suffering from and/or thought to be suffering from AD.

As will be recognized by a person of ordinary skill in the art, the chelator must be bound to the nanoparticle in a manner to retain biological activity and limit steric hindrance. After conjugation the mobility of the chelator may decrease and steric hindrance may increase, which may result in reduced iron binding affinity, especially for bidentate iron chelators. In addition, the chelators on the chelator nanoparticles may react with chelators conjugated to other particles, resulting in particle congregation. Such congregated particles may lose the ability to carry metals out of the brain. Hence, a person of ordinary skill in the art, using the guidance of the invention, may optimize the chelator and/or chelator nanopaticle to resolve such problems. For example, hexadentate chelators may be conjugated to nanoparticles, such chelators form one chelator to one iron complexes and are generally nontoxic.[51] Longer linkages, or linkages utilizing alternative structures, may be used to conjugate chelators with nanoparticles, thereby increasing mobility and decreasing steric hindrance. Another method that can be used is to first adsorb a carrier molecule with available surface functional groups, and then covalently attach the chelators to surface functional groups on these carrier molecules and/or nanoparticles. The invention includes biocompatible polymeric nanoparticles with optimal functional linkers for chemically bonding one or more chelator, for example, an iron chelator. More importantly, the nanoparticle and/or linker can also be used to optimize the particle surface properties, hence increasing the targeting and penetration abilities.

Further, additional molecules (adaptors) may be added to either the chelator or the nanoparticle. In particular, carbon chains or other linkers may be covalently attached between the chelator and the nanoparticle.

As will be recognized by a person of ordinary skill in the art, particle size, surface properties, and surface coating materials may also affect the distribution, penetration and/or toxicity of the chelator nanoparticle system, but using the guidance of the specification, the particle size and coating materials may be optimize. For example, the surface properties may be optimized by changing chelators and linkages. For example, the surface hydrophilicity/lipophilicity properties may be to alter organ distribution.[58-60] It is believed that after the nanoparticle system is able to cross the BBB and target the brain.

It is known that the lipoprotein ApoE, transports the highly water-insoluble lipid in the brain through the LDL-receptors. Without wishing to be bound by theory, this may be the mechanism by which the nanoparticles deliver drugs into brain, for example, the nanoparticles may preferentially absorb ApoE.[61-62] It is also known that ApoA-I facilitates the removal of this lipid from the brain. Therefore, by optimizing the surface lipophilic/hydrophilic property of the nanoparticle-chelator system by changing chelators, linkages, and surface coating materials to increase the ApoE absorption, the systems may be used to efficiently target the brain and cross BBB. Such systems may be designed such that after chelating iron or other metals they preferentially absorb ApoA-I and, hence, leave the brain more efficiently.

After determining the protein-absorption patterns of the systems before and after chelating metals, the systems that have better brain targeting and BBB crossing properties are identifiable.

As discussed herein, a chelator may have a higher affinity for one metal, but will still have an affinity for other metals. This has been considered the cause of much of the toxicity observed with chelation therapy. However, because it is desirable to remove all excess Fe, Al, Cu, and Zn in the brain of AD patients, the chelator nanoparticles of the invention are particularly useful in the treatment of diseases such as AD.

Typically the chelators that used herein possess high specific affinity to iron as well as to Al. They also have appreciable affinity to Cu and Zn. This feature of using one chelator to simultaneously chelate several metals, which are possible causes of AD pathology, affords the promise of easier synthesis, lower price, low drug interaction, and convenient administration.

As will be apparent, the chelator nanoparticles of the inventon may also be beneficial for other diseases, such as Parkinson's disease and Friedreich's ataxia, etc., and other diseases where excess metal ions have a role in the disease pathogenesis.

To demonstrate the pathological role(s) of excess iron in bone, and in the development of bone loss, an ovariectomized (Ovx) rat (a model of peri- and postmenopausal osteoporosis due to estrogen deficiency) model was used to demonstrate the effect of chelation therapy. The chelator synthesized for many of these tests (shown in Example X, an amphaphilic chelator possessing oral bioavailability and bone targeting activity) has a high iron binding affinity (Martell A E, Smith R M. Critical stability constants. 1974 New York, Plenum Press) and the ability to effectively deplete heavy metals such as americium and plutonium from skeleton tissues and the body of experimental animals (Miller et al.). The results show that iron accumulated significantly, with a 22.2% increase (FIG. 1), in the bone of ovariectomized rats, compared with sham operated controls, which is consistent with the result of osteoporotic human bone and osteopenic animal bone measured by EPR. In contrast, the iron content in Ovx rats treated with chelator is only 59.8% of that of Ovx rats without chelation treatment and 73.0% of that of sham controls (FIG. 1). These results indicate that chelation therapy significantly reduces iron accumulation, not only in the bone of ovariectomized rats due to estrogen deficiency, but also in the bone of aged sham control rats.

Figure 2:
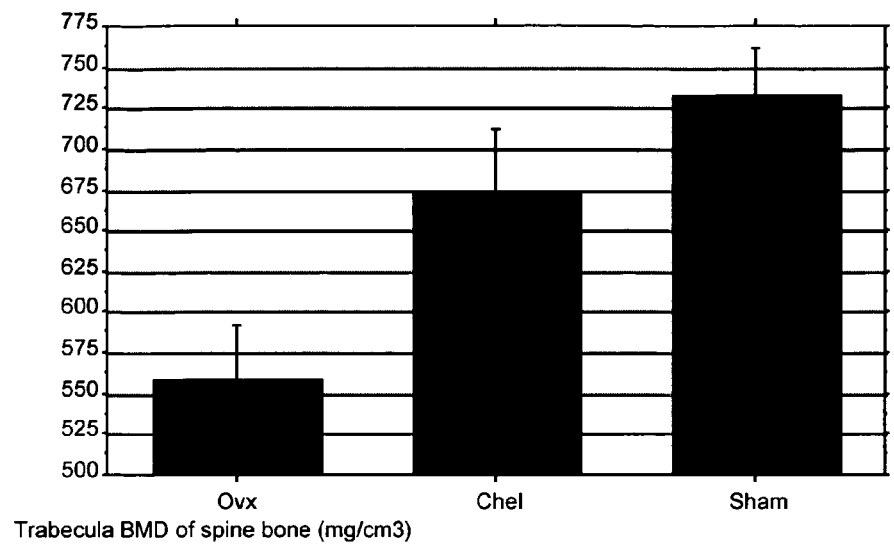
FIG. 2. (A) Trabecula BMD of spine bone. The BMD of Chel and Sham groups are significantly higher than that of Ovx group with ANOVA ($p<0.01$) and BMD of Sham group is higher than that of Chel group ($p<0.05$ by ANOVA). Each group contains 6 rats. (B) Total BMD of spine bone. The BMD of Chel group is significantly higher than that of Ovx group with ANOVA ($p<0.05$) and BMD of Sham group are significantly higher than that of Chel and Ovx groups ($p<0.05$ by ANOVA). Each group contains 6 rats.
Figure 2:
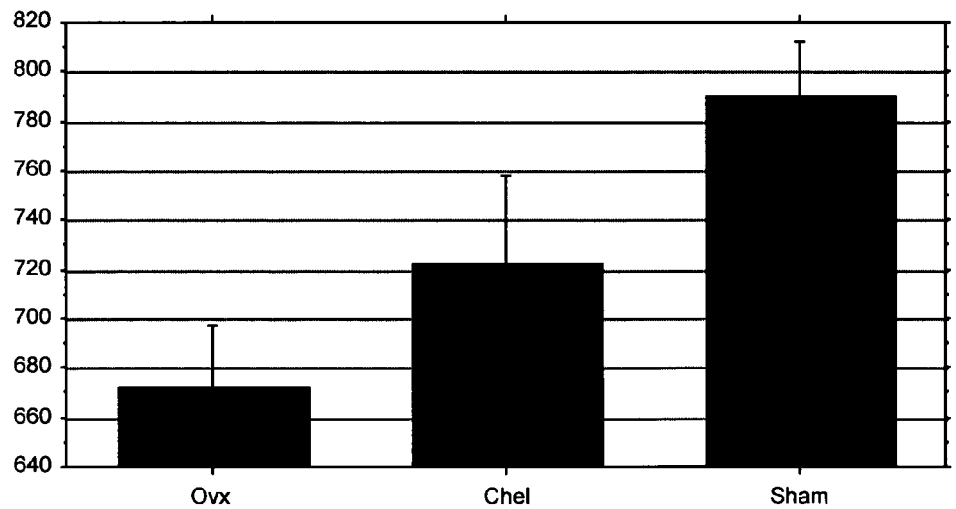

Most importantly, as expected, the reduction of iron content in the bone of Ovx rats, produced by chelation treatment, mitigates the development of osteopenia. This mitigation was demonstrated by the measurements of bone mineral density (BMD), using peripheral computed axial tomography (pQCT), and bone microstructure, using micro-computed tomography (Micro-CT). Because trabecular bone is more sensitive to develop osteoporosis caused by estrogen deficiency, the lumbar vertebra BMD was examined first. The result shows that both total and trabecular BMD of lumbar vertebra from Ovx rats treated with chelator are significantly higher than that of Ovx rat controls (FIG. 2). For the Ovx rats, the trabecular BMD of the spine lost 23.8%, compared with sham control, while the BMD of Ovx rats treated with chelator was just 8.2% less, but 20% higher than that of sham control and Ovx rats, respectively.

The present invention may be applied to the prevention of aging and aging related diseases, since iron accumulation in the body is a natural process as human ages. The present results provide new alternative approaches to the diagnosis and manage of postmenopausal osteoporosis, diseases associated with iron and other age-related diseases.

In addition to the conditions described for postmenopausal women, there is substantial evidence that in extreme iron overload conditions, damage to the skeletal system results from iron accumulation and free radical formation. For example, osteoporosis is associated with iron overload conditions, as is heart disease. Osteoporosis is common in both idiopathic and secondary hemochromatosis, presumably due to catalyzed free radical oxidative damage. Adults and children with thalassemiaa iron loading also have substantial and significant skeletal defect. Thus, substantial evidence exists in extreme iron-overloaded conditions of substantial skeletal problems associated with the iron overload.

Further supporting the involvement of iron in disease progression, studies have found iron inside the osteoblast and osteoclast and along the trabecular bone surface in iron nitrilotriacetate (Fe-NTA) overloaded animals. Indeed, vitamin E, an antioxidant, suppresses lipid peroxidation and prevents the Fe-NTA induced impairment of bone.[63] Also, histomorphometric evaluation shows that the osteoblast perimeter, as well as, the bone formation rate, decrease in chronic liver disease patients having a higher concentration of iron in their bone, relative to patients with a low bone iron concentration. Hence, the showing that chelation therapy reduces bone lose in a postmenopausal osteoporosis model indicates that the chelation therapy may also be used to treat other iron and/or metal related diseases.

In an exemplary embodiment, the invention demonstrates that chelation therapy not only maintains the bone mass but also prevents bone architectural deterioration in ovariectomized rats, wherein the ovariectomized rat model is an accepted animal model for bone loss faced by postmenopausal women due to estrogen deficiency. Based on these findings, but without being bound by theory, it is possible that the mechanism of the chelator action in mitigation of the development of bone loss is by protection against iron accumulation in bone after estrogen deficiency and aging, although other mechanisms may also be involved. For example, it is reported that EDTA chelation therapy is beneficial to bone growth for patients with some degree of osteoporosis. The present invention may explain the effect of EDTA chelation therapy. It is believed that EDTA therapy temporarily decreases the levels of serum calcium, which, in turn, stimulates parathormone production, leading to release of Ca from metastatic Ca deposits and conversion of preosteoblast to osteoblast. The chelator may also affect the action of lipoxygenase, an iron containing enzyme, as inhibition of lipoxygenase reportedly improved the BMD in an estrogen-deficient animal model.

On the basis of the findings described herein, iron accumulation in bone is associated with osteoporosis and osteopenia in estrogen deficient women and animals. The accumulation of iron plays a causal role in the development of bone loss, demonstrated by purging iron from bone of Ovx rats with an iron chelator, thereby retaining bone mass and preventing structural deterioration of the bone.

The present invention teaches a model of oxidative damage to the skeleton, which is consistent with some studies showing that antioxidants have a protective effect on bone loss caused by estrogen deficiency.[72 but cf 73] The present demonstration of a new pathway in the development of postmenopausal osteoporosis provides an approach to the prevention and/or treatment of diseases by preventing iron accumulation and oxidative damage in the body. Thus, an exemplary embodiment of the present invention contemplates the use of an iron chelator, an antioxidant or a combination thereof in the treatment of disease.

As will be recognized by the person of skill in the art, this is very important because there is a great deal of controversy regarding hormonal replacement therapy for postmenopausal osteoporosis.

EXAMPLE I

Iron accumulation in osteoporotic bone of postmenopausal women was measured by EPR spectroscopy of femoral cortical bones from aged women, using Inductively Coupled Plasma Optical Emission Spectroscopy (ICP-OES). Three osteoporotic bone samples, each from three postmenopausal women, were examined. Three additional bone samples from three postmenopausal women without osteoporosis were also examined as age-matched controls. It was found that the total iron content in the bone of postmenopausal women with osteoporosis, with a mean value of 25.8 ppm±5.6 (standard deviation), are significantly higher (Paired t test, P<0.01) than that of postmenopausal women without osteoporosis (6.5 ppm±2.3). This observation further demonstrates the association of increased iron content in osteopathic bone of postmenopausal women and is consistent with the demonstration of increased free iron, assessed by EPR, in the osteopathic bone of postmenopausal women.

In postmenopausal women the levels of stored iron, which represents a potentially powerful catalyst for free radical formation, increase significantly, while estrogen levels, which represents a potential antioxidant, decrease dramatically. Hence, the physiological changes associated with menopause increase a woman's risk of free radical damage. Examples of serum ferritin (a indicator of body iron status) and estradiol levels before and after menopause are presented in Table 1. Ferritin levels with iron overload are also included for comparison.

TABLE 1

Mean serum ferritin and estrodiol concentrations in pre and postmenopausal women:

| Concentration | Before | After | Iron overload |
| --- | --- | --- | --- |
| Serum Ferritin (µg/L) | 39.8 [10][46] | 108.6 [10] | 200 [39] |
| Estrodiol (pmol/L) | 200–600 [11] | 50 [11] | |

EXAMPLE II

Figure 3:
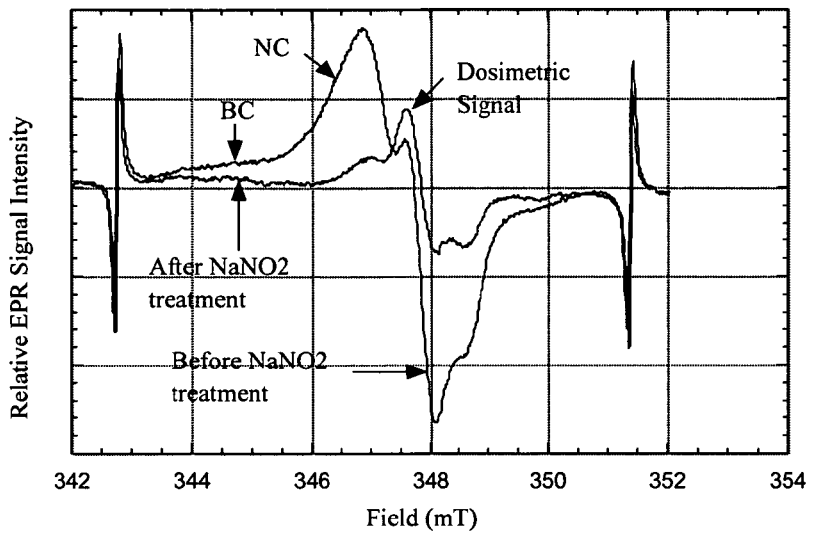
FIG. 3 (left). EPR spectra of canine cortical midshaft bone before and after treatment with sodium nitrite.
Figure 4:
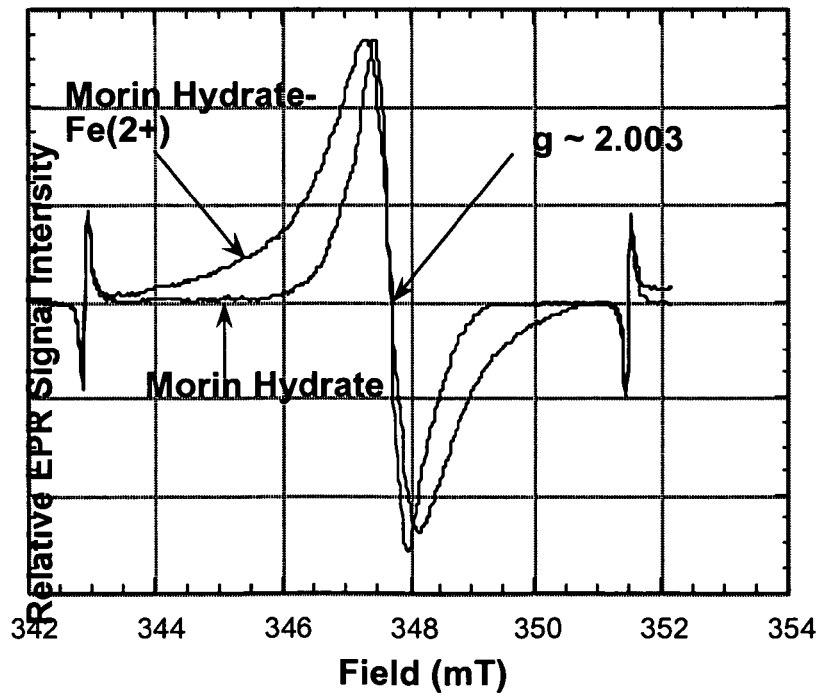
FIG. 4 (right). EPR spectra of morin hydrate and morin hydrate-$Fe^{2+}$ complex following the reaction of morin hydrate with ferrous sulfate.

EPR techniques were used to detect free iron and LLOFR, as a marker of oxidative damage. This approach has been used by others to assess similar events in soft tissues. Briefly, the iron signal, a broad component (BC) of the EPR native signal of bone (FIG. 3) was identified by comparison of the signal generated by reacting an organic entity which is commonly found in biological tissues with iron (FIG. 4). The original EPR signal of iron (BC) disappears upon treatment (FIG. 3) of bone granules with sodium nitrite that reacted with free iron to form specific iron-nitric oxide complexes. Furthermore, the narrow component (NC) (FIG. 3) is responsible for the LLOFR that is oxidized organic compounds and stable in some solid matrix, such as bone, seeds and plants. The NC is indeed identical with the EPR signal of stable organic free radical produced by morin hydrate due to oxidation (FIG. 4).

To demonstrate the reverse effect, the reaction of ferrous sulfate with morin hydrate was used. The results are shown in FIG. 4. Morin hydrate is a representative of the semiquinone class of compounds which are found in numerous enzymes. It can be seen that unreacted morin hydrate has a NC while the ligand bound morin hydrate-iron complex has a BC.

Figure 11:
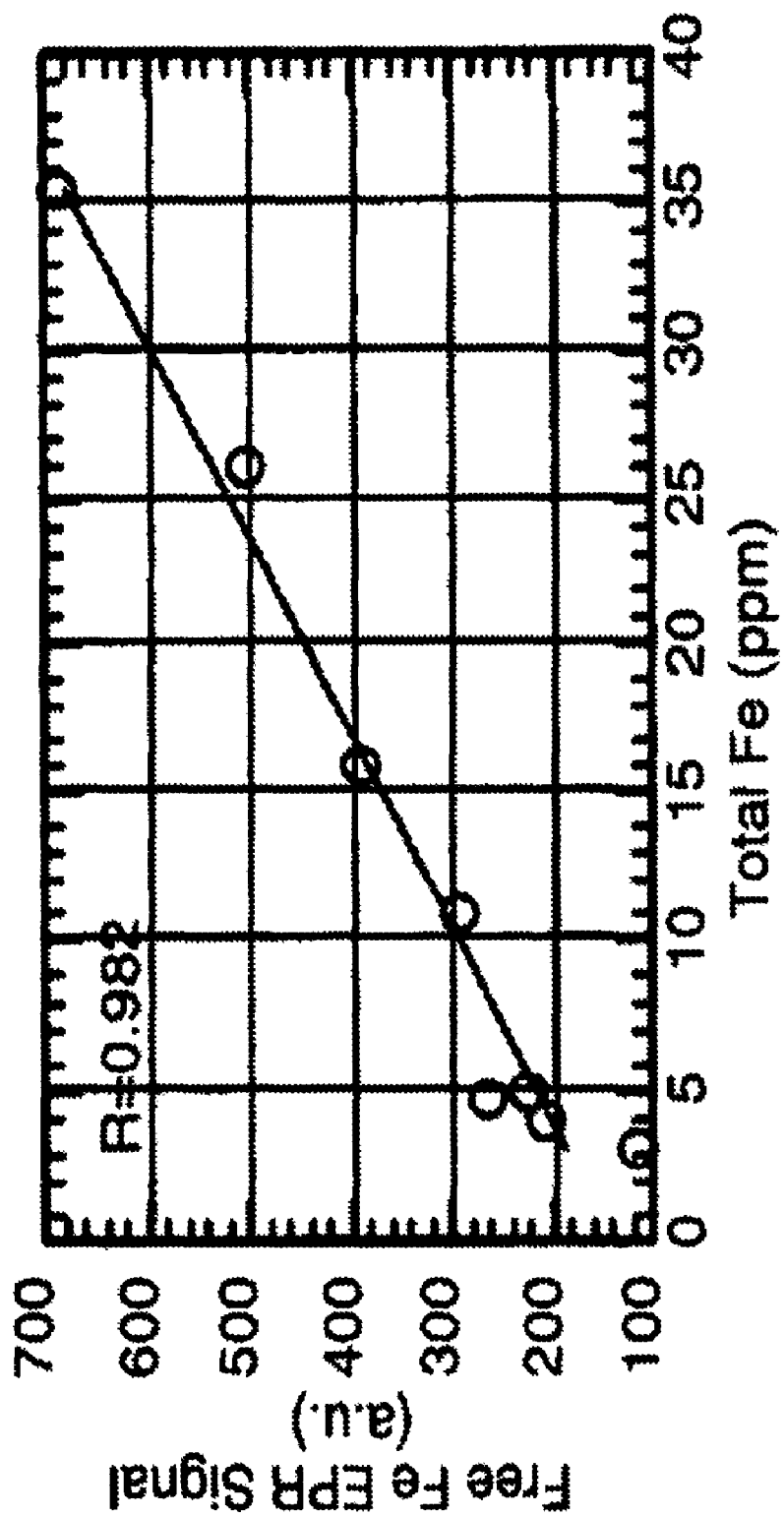
FIG. 11 shows a graph of iron contents of human femoral cortical bone detected by EPR spectroscopy (free iron) (Y) and measured by GFAAS (total iron) (X).

The free iron contents detected by EPR are positively proportional to total iron concentrations in bone, as measured by graphite furnace atomic absorption spectroscopy (GFAAS). This relationship indicates that total iron accumulation increases the availability of free iron in bone consequently causing oxidative damage. This relationship is presented in FIG. 11.

The EPR technique allows for simultaneous measurement of free iron and LLOFR in bone and is convenient and repeatable. Most importantly, EPR spectroscopy is very sensitive to very small amounts of paramagnetic materials, which could be as little as femtomoles. However, it should be noted that the absolute values of iron and LLOFR could not be determined by this method. Although the relative values do provide enough information to determine the effects of chelation therapy. In addition, a free radical standard in bone matrix is developed to assess the amounts of free iron and LLOFR. Most importantly, the EPR technique is used as a non-invasive diagnostic tool for early detection of postmenopausal osteoporosis.

EPR-osseous tissue sample preparation and measurement: Samples of human femoral cortical bone preserved in 70% alcohol were initially crushed into large pieces (<1 mm) using a mortar and pestle. The granules were defatted with 10 changes of acetone and dried at 60° C. The samples then were further crushed and sieved to obtain a 250-600 micrometer fraction. The EPR measurement of approximately 100 mg of sample were made at 24° C. with values for g-factors of 2.00503±0.00019 (NC) and 2.00541±0.00085 (BC) and with widths of 0.916±0.0465 mT (NC) and 2.5 mT (BC) following a modification of known protocols.[74-75] A Bruker 300E spectrometer at 9.7 GHz was used for date collection.

Measurement of total Fe contents in bone by GFAAS: The same bone samples used for the EPR measurements were used for this assay. Each sample of about 100 mg was mixed with 5 mL of 70% nitric acid solution (99.999% pure) in a polypropylene sample tube with a hinged cap (CPI international, Santa Rosa, Calif.) and then digested at 60° C. for 2 hours. The solution was diluted with Milli-Q water and exactly transferred into a 10 mL volumetric flask. The tube was washed several times with Milli-Q water, which was collected into the volumetric flask. The solution was diluted to 10 mL with Milli-Q water and aliquots were analyzed for Fe using a Perkin-Elmer 3100 Graphite Furnace spectrometry. Pyrex or other glasses must be pre-washed by acidic solution to avoid iron contamination. 2% Nitric Acid standard iron solutions are prepared for the GFAAS analysis.

Increased free iron and LLOFR levels in bones of postmenopausal women with osteoporosis compared to age-matched control: Using EPR spectroscopy of human femoral cortical bone, it was determined that the free iron (BC) and LLOFR(NC) signals change in response to estrogen status and severe intracortical bone loss in human females. Bone from the upper midshaft (70% line) of femora from young (17-34 years old, n=5) and elderly (70-92 years old, n=16) females were examined. The results showed that the elderly women had significantly higher BC and NC in bone than that of the younger women (Table 2). This revealed that the status of endogenous estrogen levels indeed affects the free iron levels and oxidative damage in the bones of females. With the high concentration of estrogen in young females, estrogen may play an important role in protection against iron accumulation and oxidative damage in bone, while in elderly females this protection declines due to estrogen deficiency. The increased iron accumulation and oxidative damage associated with estrogen deficiency may induce the gradual bone loss (osteopenia) in elder females. Osteoporosis will take place if iron and oxidative damage levels are too high. This is supported by the following analysis. In the same group of 16 elderly females, we examined the BC and NC of the periosteal cortical bone of three women, whose endosteal intracortical bone was severely porotic, and compared this with that of the other 13 women. It was found that the BC and NC of the elderly females are significantly higher at the P<0.05 levels (Table 2). The total iron levels in the bones of the elderly females with osteoporosis measured by GFAAS were also found to be significantly higher than that of age-matched women as a further confirmation.

TABLE 2

Changes in the magnitudes of free iron (BC) and LLOFR (NC) components of EPR signal of bone from aging females:

| Cortical bone of midshaft | (n) | BC (a.u./mg) | NC (a.u./mg) |
|---|---|---|---|
| 17–34 years old | (5) | 200.4 ± 68.95 | 999 ± 506.25 |
| 60–92 years old | (16) | 307.39 ± 78.96* | 1673.63 ± 201.34* |
| 60–92 years old | (13) | 273.76 ± 26.16 | 1613.15 ± 116.84 |
| Osteoporosis | (3) | 453.1 ± 58.83* | 1935.67 ± 308.81* |

Values are mean ± S.D. t-test statistics.
*Significantly different from control group, $p < 0.05$.

Femoral cortical bones of aged women were examined for iron contents by GFAAS. Three osteoporotic bone samples, each from three postmenopausal women were used. One woman was 84 years old and other two were 92 years old. Three normal bone samples from three postmenopausal women without osteoporosis were examined as age-matched controls. The age-matched controls were 82, 86 and 90 years old. The iron concentrations in the bones of postmenopausal women with osteoporosis are significantly higher than that of postmenopausal women without osteoporosis. The results are presented in Table 3.

TABLE 3

Total iron contents in bones of females with postmenopausal osteoporosis and age-matched controls:

| Cortical bone of midshaft (n) | Total Fe (ppm) Mean ± SD |
|---|---|
| Osteoporosis (3) | 25.8 ± 9.7* |
| Age Matched (3) | 6.5 ± 4.03 |

Values are mean ± S.D. t-test statistics.
*Significantly different from control group, $p < 0.01$.

EXAMPLE III

Histomorphometric analysis is performed on bone samples, for example, bone samples from Examples I and II may be used. Histomorphometric analysis provides information on bone structure, bone turnover and bone remodeling affected by increased iron, free radical damage and the effects of chelation therapy. Histomorphometric analysis is particularly valuable in analyzing the cellular pathophysiology of different forms of osteoporosis and in determining the mechanisms by which drugs affect bone.

This analysis is found to support the role of oxidative damage in the skeletal system. Thus, chelation therapy is found to provide a method to protect against postmenopausal osteoporosis and/or diseases associated with increased metals, such as iron, and free radical damage. For example, diseases associated with increased metals include, but are not limited to, senile and aging osteopenia in both men and women, as well as, neurodegenerative and heart diseases related to sex-hormone deficiency and aging may be treated.

EXAMPLE IV

The OVX rat model is a well-established and documented model of peri- and postmenopausal estrogen-deficiency dependent bone loss, because ovariectomy induced bone loss in the rat and postmenopausal bone loss share many similar characteristics. These include an increased rate of bone turnover with reabsorption exceeding formation, an initial rapid phase of bone loss followed by a much slower phase, greater loss of cancellous than cortical bone, decrease intestinal absorption of calcium and some protection against bone loss by obesity. Also, there is similar skeletal response to therapy such as estrogen, bisphosphonate, parathyroid hormone, calcitonin and exercise. One possible limitation of the ovariectomized rat model is that, unlike human skeleton, rat skeleton may lack the Haversian systems and does not remodel. However, studies have showed that cancellous bone remodeling activities exist in several sites of the rat skeleton, such as vertebrae, alveolar bone and the mandibular periosteal surface. The remodeling activities at these sites are strikingly similar to that of adult human cancellous bone.

The above results in human were confirmed in an ovariectomized (OVX) rat model. The Ovx-rat model was used because the ovariectomy makes the rats estrogen deficient and accelerates bone loss, similar to the bone loss observed in women following menopause. Comparison of the data generated by this method provides evidence that loss of estrogen causes increased iron accumulation and oxidative damage and that these increases are related to bone loss.

Humeral bones from four groups of 3 or 4 rats (Sprague-Dawley, Charley River) each were evaluated. The baseline group consisting of 3 normal rats were sacrificed at six months of age using Ketamine-Xylazine anesthesia. The other three groups (4 rats each) were sham ovariectomized (SHAM) (one group) or ovariectomized (OVX) (two groups) at the same age. Bilateral ovariectomy was performed using a dorsal approach under aseptic conditions with Ketamine-Xylazine anesthesia.[76] One group of OVX animals was treated by estradiol IP injection with 10 μg/kg body weight of 17b-estradiol in benzyl alcohol/corn oil solution (5:95, vol/vol). The injections were three times a week. The other two groups (SHAM and OVX controls) received the oil solution without estradiol. All groups were sacrificed at 60 days post-surgery. No difference for BC and NC was seen between the baseline controls and the SHAM group. A significant increase ($P<0.05$) was seen in the BC (free iron) and NC (LLOFR) of the OVX rats compared with the SHAM animals. Most importantly, with estradiol treatment of OVX rats, the levels of BC and NC in bone were reduced to levels similar to those observed in the SHAM controls. The changes in BC and NC were attributed to increases in the iron content and LLOFR of the tissue component responsible for the EPR signal (Table 4).

TABLE 4

Free iron (BC) and LLOFR (NC) of the EPR signal of humeral bone from rats:

| Cortical bone of midshaft | (n) | BC (a.u./mg) | NC (a.u./mg) |
|---|---|---|---|
| Baseline | (3) | 223.8 ± 17.4 | 1150 ± 81.0 |
| Sham Control | (4) | 204.9 ± 21.4 | 1224.8 ± 101.7 |
| OVX | (4) | 316.2 ± 19.2[a] | 1669.5 ± 66.9[a] |
| OVX Estrogen | (4) | 214.3 ± 11.1[b] | 1357.5 ± 101.4[b] |

[a]Significantly different from shame controls, $P < 0.05$.
[b]Significantly different from OVX, $P < 0.05$.

The results from both human and animal studies demonstrate that estrogen deficiency results in increased iron accumulation and oxidative damage. Estrogen therapy for OVX rats protects against these increases. Protection by estrogen was found in both young women and estrogen treated rats.

EXAMPLE V

To address whether the increased levels of iron and oxidative damage in bone are causative factors leading to the onset of osteoporosis associated with estrogen deficiency or the consequence of the disease process, an iron chelator targeted to bone was used to treat OVX rats. Under the hypothesis being tested, if the increased iron levels and iron catalyzed oxidative damage are a causative factor in the development of bone loss, reducing the iron levels, by removal iron using chelation therapy, will mitigate the bone loss.

Animal and treatment: Three-month-old female Sprague-Dawley rats (Charles River Laboratory) were obtained and housed with a 12 h light-dark cycle at constant room temperature (24° C.) and humidity. The rats were fed standard rat chow (#8640 Harland Teklad, Madison, Wis.) and water ad libitum. When aged 6 month, the rats were divided into four groups. One group was sacrificed as baseline controls at the beginning of the experiment. The remaining groups were sham operated (one group) or bilaterally ovariectomized (two groups) via a dorsal approach. Chelation treatment started from the second day after surgery and was given three times a week for 9 weeks. The chelator (1-N-Docosyltriethylenetetraminepentaacetic acid, GL22) was dissolved in saline (pH 7.5) and was administrated by oral gavage (100 μmole/kg), while control groups including the sham and Ovx operated animals received vehicle only in the same manner.

Fluorochrome bone markers calcein (fluorescein-methylene-iminodiacetic acid, 10 mg/kg body weight) and tetracycline-HCl (25 mg/kg body weight) from Sigma Chemical Co. were given by interperitoneal injections on 10 and 3 days, respectively, prior to necropsy for later evaluation of bone dynamics by histomorphometry. The rats were anesthetized and sacrificed via cardiac puncture. Humeral bone and Lumbar vertebrae were dis-articulated and surrounding tissue was manually dissected.

Tissue preparation and analyses: Humeral bone was fixed in 70% ethanol for measurement of tissue iron by EPR. Lumbar vertebrae were first fixed in 10% phosphate buffered formalin for 24 hours, then dehydrated in ascending concentrations of ethanol and embedded in methyl methacrylate. The blocks were trimmed for peripheral computed tomography (pQCT), micro-computed tomography (μ-CT) and later prepared for histomorphometric studies.

pQCT densitometry: The L3 vertebra bodies were examined by pQCT densitometry (Norland Stratec XCT 960A, Birkenfeld, Germany) to determine bone mineral density (BMD) for the part from the middle point to the caudal end, excluding the primary spongiosa. A scout scan of the vertebra was performed, and on the scout view, a reference line was manually placed such that the cross-sectional slice passed through at a distance of 1, 2, 3 and 4 mm from caudal end of lumbar vertebra body. The voxel size was 196 µm. Contour mode 2, Peel mode 20, Cortical mode 2 and threshold 570 for cortical bone was chosen for the analysis. The mean BMD for all of the measured slices was then calculated.

µ-CT measurement: Lumbar vertebra were scanned in all three dimensions with a high-resolution µ-CT (10 µm) (Scanco µCT-40, Scanco Medical, Bassersdorf, Switzerland). The complete third vertebral bodies were scanned with 600 slices, each containing 2048×2048 pixels. The trabecular and cortical part of the bodies were separated with semi-automatically drawn contours. The resulting grey-sclae images were segmented using a low-pass filter to remove noice and a fixed threshold to extract the mineralized bone phase. From the binary images, structural indices were assessed with three-dimensional techniques without model-assumptions of the appearance of trabecular bone and were calculated by measuring three-dimensional distances directly in the travecular network and taking the mean over all voxels. The region of interest was travecular bone in the lumbar vertebral body, excluding the prmary songiosa area, 0.5 mm from the growth plate.

Iron measurement: Total iron contents of femoral cortical bones of aged women were assessed using ICP-OES performed by Galbraith Laboratories, Inc. (Knoxville, Tenn.). Samples preserved in 70% alcohol were initially crushed into large pieces (<1 mm) using a mortar and pestle, then were further crushed and sieves used to obtain the 250-600 micrometer fraction. Each sample of about 100 mg was mixed with acid solution, microwave digested and measured. Free iron contents in humeral cortical bone of rats were assayed by EPR spectroscopy. Samples were crushed into pieces (<1 mm) using a mortar and pestle. The granules were defatted with 10 changes of acetone and dried at 60° C. The samples were then further crushed and sieves used to obtain the 250-600 micrometer fraction. The EPR measurement of approximately 100 mg of sample were made at 24° C. with values for g-factors of 2.00503±0.00019 (NC) and 2.00541±0.00085 (BC) and with widths of 0.916±0.0465 mT (NC) and 2.5 mT (BC) following a modified protocol (Kenner et al. (2005) Variation of long-lived free radicals responsible for the EPR native signal in bone of aged or diseased human females and ovariectomized adult rats, *Radiat. Meas.* 39:255-262). A Bruker 300E spectrometer at 9.7 GHz was used for date collection.

Chelator synthesis: The synthesis was described previously.[39-40] Briefly, a primary amino group of triethylenetetramine was alkylated with 1-docosyl bromide, followed by exhaustive carboxymethylation of the remaining amino groups using ethyl bromoacetate with subsequent hydrolysis of the ester. The chelator was characterized and the structure confirmed using IR spectroscopy, $^1$H-and $^{13}$C-NMR and mass spectrometry. The chelator was prepared as a HCl salt. The chelator, called GL22, has the following basic structure:

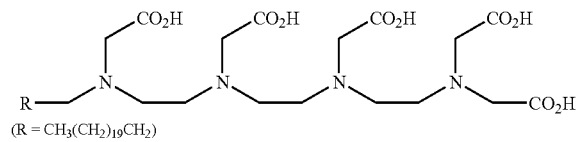

(R = CH$_3$(CH$_2$)$_{19}$CH$_2$)

Statistics: Results are expressed as a mean±standard deviation (SD). Statistical analyses of the data were carried out using the Statview Statistical Package (Abacus Concepts, Inc., Berkeley, Calif.).

Figure 5:
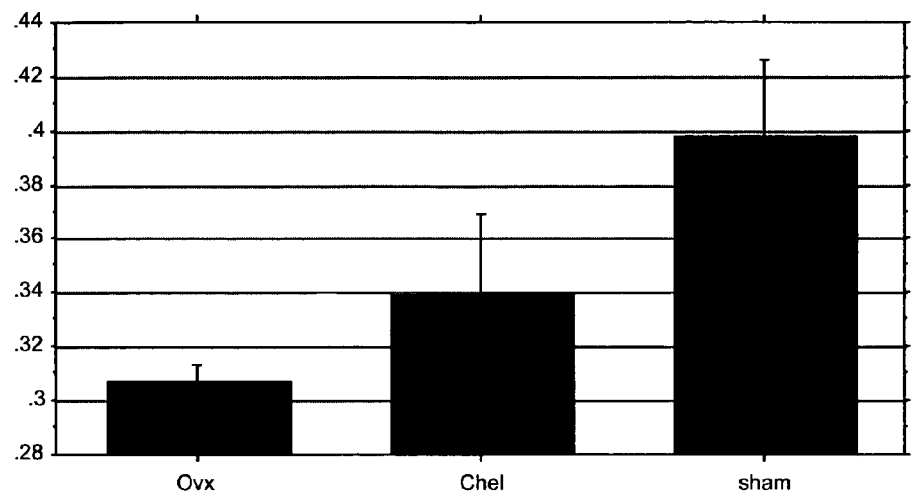
FIG. 5. Morphological index of spin bone from groups of Ovx, Chel and Sham rats ($n=6$ per group). (A) Ttrabecular bone volume/Total volume measurements are significantly different between the three groups with $p<0.05$ by ANOVA. (B) Ttrabecular bone separation measurements are also different significantly between the three groups with $p<0.05$ by ANOVA.
Figure 5:
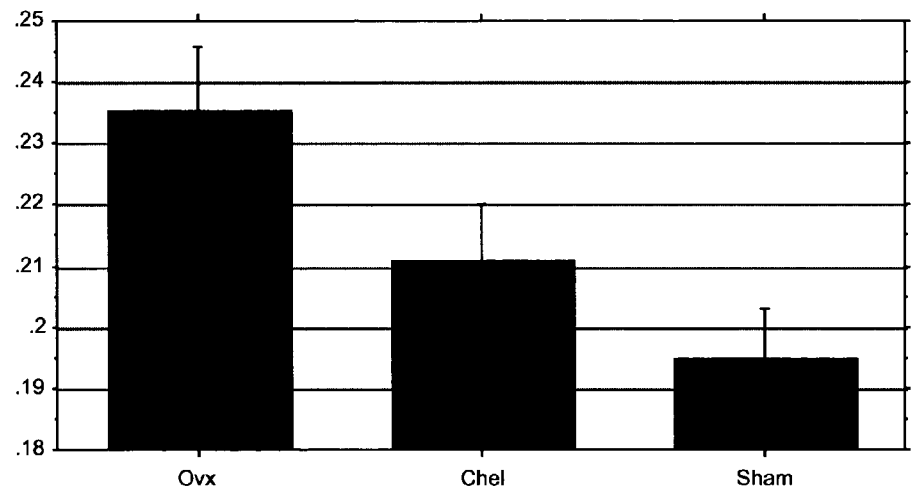
Figure 6:
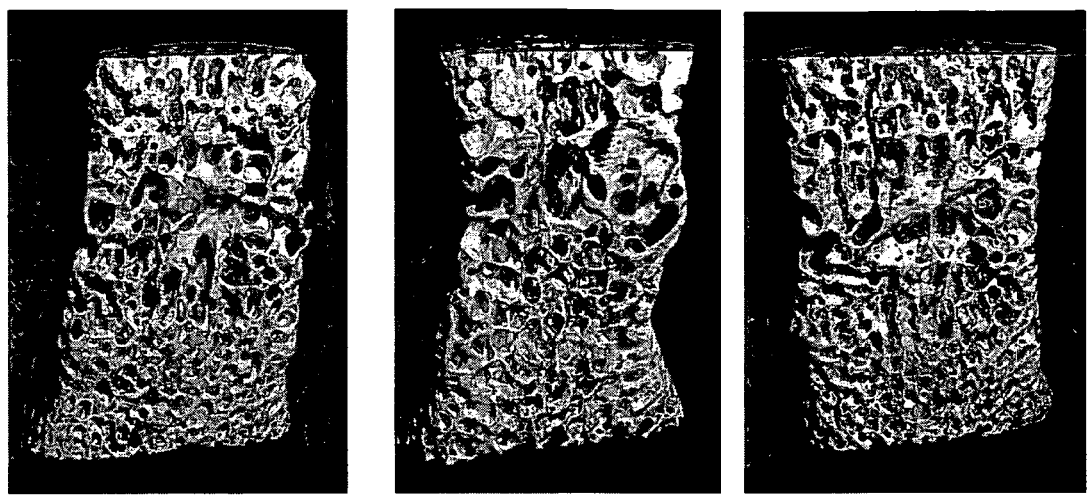
FIG. 6. Micro-CT images of spin bone from groups of Ovx, Chel and Sham rats ($n=6$ per group). The three-dimensional reconstruction images demonstrate the micro-architectural differences between the groups.

The structure of the cancellous bone was also examined using µ-CT and the morphological measurements derived. The ratio of bone volume to tissue volume (BV/TV) in chelator-treated Ovx rats treated was significantly higher (9.1%) than that of untreated Ovx rats, which indicates more trabecular bone in chelator treated Ovx rats. At the same time, the trabecular separation (Tr. Sp.) was significantly less (10.2%) in chelator-treated Ovx rats compared with OVX controls. This result also showed increased marrow spaces in Ovx rats without treatment. The micro-CT images (FIG. 6) further demonstrate increased trabecular bone volume and decreased marrow space in the bone of Ovx rats treated with chelator compared with untreated Ovx rats. It should be mentioned that the trabecular BMD and BV/TV of Ovx rats treated with chelator are less, 91.8% and 85.2%, respectively, compared with sham control, while the Tr. Sp. is higher, an 8% increase (FIGS. 2 and 5).

Taken together, the age-associated iron accumulation in bones of CVX rats may play a significant role in the development of bone loss associated with estrogen deficiency. This association is further supported by the observation that by limiting and/or reducing the free iron concentration in bon by iron chelation, there was a significant retention of bone mass and a slowing of the deterioration of bone structure. The skeletal protection associated with iron reduction by chelation was due to a significant reduction in bone reobsorption and perhaps a maintenance or an increase in bone formation after ovariectomy.

In another experiment, four groups of 3 or 4 rats (Sprague-Dawley, Charley River) each were used. The baseline group consisted of 3 normal rats, which were sacrificed at six months of age. The humeral bones were collected for EPR free iron and LLOFR measurements and the whole body bone mineral density (BMD) was assessed by Dual x-ray absorptiometry (Hologic QDR1000 Plus) before necropsy. The other three groups were sham ovariectomized (one group) or ovariectomized (two groups) at the same age. The operation (a dorsal approach of bilateral ovariectomy) was under aseptic conditions with Ketamine-Xylazine anesthesia. One group of OVX animals was treated by chelation therapy with 30 µmol/kg body weight of GL22 in saline solution (pH 7.5). The GL22 was orally administered by intubation with a blunt-ended stainless steel needle three times a week. The other two groups received the saline solution without chelator by the same manner. All groups were sacrificed at 60 days post-surgery to collect humeral bones for EPR free iron and LLOFR measurements. Before the termination, whole body BMD was measured. The results of the EPR measurements showed that the free iron and LLOFR levels in bones of chelator-treated OVX rats were significantly lower than that of OVX rats and similar to that of SHAM rats. These results are presented in Table 5. Most importantly, the whole-body BMDs of chelator-treated OVX rats were significantly higher than that of OVX rats and remained the same as that of SHAM rats (Table 5). These results indicated that reducing iron and oxidative damage levels by iron chelation therapy prevented bone loss associated with estrogen deficiency, which strongly support the hypothesis that increased iron and oxidative damage levels are a causative factor leading to osteoporosis.

TABLE 5

Free iron and LLOFR levels in bones and whole body BMD of female rats:

| Cortical bone of midshaft | (n) | BC (a.u./mg) | NC (a.u./mg) | BMD (g/cm2) |
|---|---|---|---|---|
| Baseline | (3) | 223.8 ± 17.4 | 1150 ± 81.0 | 0.175 ± 0.003 |
| Sham Control | (4) | 204.9 ± 21.4 | 1224.8 ± 101.7 | 0.189 ± 0.004 |
| OVX | (4) | 316.2 ± 19.2[a] | 1669.5 ± 66.9[a] | 0.169 ± 0.007[a] |
| OVX GL22 | (4) | 202.7 ± 32.9[b] | 1083 ± 127[b] | 0.188 ± 0.004[b] |

[a] Significantly different from shame controls, $P < 0.05$.
[b] Significantly different from OVX, $P < 0.05$.

These animal studies were performed on 6-month old rats. Studies with OVX aged rat model (12 month old) may be used to further demonstrate the results. In particular, postmenopausal bone loss of women starts after the attainment of skeletal maturity, thus, rats of sufficient age to attain skeletal maturity may be used to more fully reflect the skeletal status of postmenopausal women. Studies have showed that all the bone parameters of rats reached plateau levels by 12 month old, while changes in femur density and calcium remain at the age of 6 months.

Bone loss reduced by ovariectomy is not complicated by disease or loss of bone due specifically to aging: The use of 12 month-old rats is used to ensure that bone changes observed following ovariectomy in the aged rat model are due primarily to ovarian hormone deficiency. Different bones and bone sites may also be assayed to determine the presence of differential sensitivity to the iron catalyzed oxidative damage and responses to treatments. For example, the cancellous bone is more sensitive to estrogen deficient bone loss than cortical bone.

A variety of amphipathic chelators have been synthesized and have been demonstrated to have a high binding affinity for iron (and some other metals) and also have the ability to target bone due to their amphipathic character. GL22 is a member of this class and its synthesis was described previously. Briefly, a primary amino group of triethylenetetramine was alkylated with 1-docosyl bromide, followed by exhaustive carboxymethylation of the remaining amino groups using ethyl bromoacetate with subsequent hydrolysis of the ester. The chelator was characterized and the structure confirmed using IR spectroscopy, $^1$H-and $^{13}$C-NMR and mass spectrometry. GL22 was prepared as the HCl salt. The chemical structure of GL22 is illustrated in below. The long alkyl chain possesses the lipophilicity while the carboxylic groups hydrophilicity, which make GL22 amphipathic.

The structure of GL22 is:

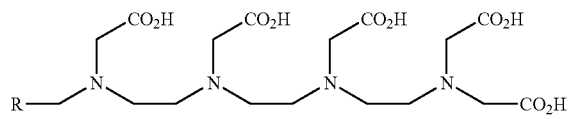

wherein R is a long chain alkyl.

This class of chelators was selected over the established iron chelator, desferroxiamine (DFO) because DFO is known to have some toxicity in the skeletal system and it does not target or penetrate bone as effectively as amphipathic compounds. Another iron chelator, 1,2-methyl-3-hydroxyl-4-pyridinone, approved in clinical use outside the USA, may be used. Thus, a person of ordinary skill in the art, using the guidance of the present specification, will understand that the chelators of the invention may be varied depending on a number of conditions and properties known in the art, for example, targeting specificity, chelator specificity for a particular metal or compound, lipophillicity and the like.

The use of this iron chelator provided a unique method to identify the causative role of iron and oxidative damage in bone loss. However, the chelator may chelate other metal ions. As will now be recognized by person of ordinary skill in the art, chelation agents include chelators that bind to different metal ions and any chelation agent appropriate for the desired target metal may be used. Depending on the metal to be chelated, potential toxicity issues may be addressed by the person of ordinary skill in the art using methods and properties known in the art.[77-80]

GL22 was not found to remove Ca from bone because the BMDs of bones from chelator-treated OVX rats were almost identical to that of SHAM rats (Table 5).

EXAMPLE VI

12 Male Sprague-Dawley rats from Simonsen Laboratories (Gilroy, Calif.) at about 80 days of age were given an intravenous injection of 241-Am-citrate in a total volume of 0.2 mL. For chelator treatment, the GL22 was dissolved in saline and the pH was adjusted to 7.5 with NaOH. Fourteen days after administration of 241-Am-citrate, a chelator food ration was started at 50 μmol/rat/day for 90 days orally, while the same food ration without chelator was given to controls. 50 μmol of chelator was added to the daily food ration (25 g). The total body retention of 241-Am was measured using a whole body-counter and after necropsy the skeletal tissues were counted for 241-Am content. The experimental protocol was described in an earlier publication. These results are presented in Table 6 and showed that the 241-Am was removed from bone tissues and the body of the rats by chelation treatment. The same results have also been found for 239-Pu. Moreover, the excretion of iron from iron overloaded male rats that were treated by chelator was tested. The same rats as above at the age of 180 days were given 10 mg of iron as iron-dextran (Sigma, St. Louis, Mo.) subcutaneously every 3 days for 6 weeks to induce iron overloading. Then, a low iron diet (Teklab diet #80396) was given to the rats for 2 weeks as the baseline iron excretion reached plateau levels, which was determined by GFAA measurement of iron in feces. The chelator treated rats were given 20 g of low iron diet with 30 μmol of GL22 and control rats were given just 20 g of low iron diet each day for 14 days. Feces were collected every day for determination of iron excretion. The samples of feces were placed in glazed porcelain crucibles, dried at 100° C. overnight and ashed in a muffle furnace at 550° C. for 18 h. The ashed feces were dissolved in 4 mL of 3 N HCl and quantitatively transferred to a volumetric flask. The crucibles were then rinsed twice with 5 ml of 0.36 N HCl. The concentration of iron was determined by GFAA spectrophotometry (Perkin Elmer). After 14 days of chelation treatment by oral administration there were significant increases in the amounts of iron found in the feces when compared with controls (Table 7).

TABLE 6

241-Am retention of percent whole body and skeletal tissue after GL22 treatment:

| ID (Number of animals) | Whole body | Femur | Humerus | Vertebral body |
|---|---|---|---|---|
| Control (6) | 66.9 ± 2.1 | 4.74 ± 0.10 | 4.80 ± 0.14 | 5.47 ± 0.17 |
| GL22 (6) | 50.8 ± 0.7* | 4.06 ± 0.08* | 3.97 ± 0.09* | 4.05 ± 0.23* |

*Significantly different from controls, $P < 0.05$ by analysis of variance with Dunnett's test for multiple comparisons.

TABLE 7

Iron excretion from feces of iron overload rats treated by GL22 compared to controls:

| ID (Number of animals) | Excreted Fe from feces |
|---|---|
| Control (n = 3) | 900.46 ± 66.99 |
| Chelator (n = 3) | 1084.62 ± 88.54 |

Significantly different from controls, P < 0.05

EXAMPLE VII

In an exemplary embodiment, estrogen therapy, treatment with an antioxidant, e.g., vitamin E, an iron chelator and/or combinations thereof, will increase the trabecular bone area, calculated trabecular thickness and number while decreasing the trabecular perimeter to area ratios and the calculated trabecular separation compared with Ovx controls. At the same time the number of trabecular nodes and struts is anticipated to be higher and the marrow star volumes smaller than that of Ovx controls. Preferably, an iron chelator and an antioxidant are co-administered to reduce iron storage and further prevent oxidative damage.

Preparation of osteopenic bone induced by ovariectomy in rats for bone mineral content (BMC), morphometric and histomorphometric studies: Two groups of 4 rats (Sprague-Dawley, Charley River) at 3 months of age were used in this study. Throughout the study, animals were fed a standard laboratory diet and had free access to food and water. One group was ovariectomized and another was sham operated. After 6 weeks the animals were terminated and left tibias and femurs were collected at necropsy. At 13 days prior to necropsy, 25 mg/kg body weight of oxytetracycline-hydrochloride (Durvet, Blue Springs, Mich.) was given by intraperitoneal injections to all animals and at 7 days prior necropsy the animals were given 10 mg/kg body weight of calcein (Sigma Chemical Co., St. Louis, Mo.). These fluorochromes were given as bone markers for histomorphometry. The femurs were kept moist in saline for determination of BMC by photon absorptiometry or pDXA (peripheral dual x-ray absorptiometry, Norland). The tibias were fixed in phosphate-buffered formalin, dehydrated in ethanol and embedded undecalcified in methyl methacrylate. Frontal sections through the proximal tibia were cut with a low speed bone saw and ground to about 100 μm in thickness and microradiographed. The sections were glued to plastic slides, ground to about 30 μm in thickness, polished and stained with toluidine blue and basic fuchsin prior viewing the fluorochromea labels. A section from each animal was surface stained with a modified Giemsa stain.

The BMC of the femurs was measured with a single photon absorptiometer (Norland Corp., Fort Atkinson, Wis.) at 11 intervals from the distal to proximal end and the mean BMC for all of the measured sites was calculated. The BMC of selected sites and the overall whole bone average BMC are presented in Table 8. These results show that the BMCs in the distal femur and all sites in the proximal femur were significantly less compared with controls, but there was no difference in the midshaft of femurs. This is because of the greater loss of cancellous bone at distal and proximal femur than cortical bone at midshaft after OVX [21].

TABLE 8

Femoral BMC and the overall whole bone average BMC expressed per bone width (BMC/BW):

| Distance from distal to proximal end | Control BMC/BW (g/cm/cm ± SE) | Ovx |
|---|---|---|
| ⅛ inches (Distal) | 0.320 ± 0.005 | 0.288 ± 0.006* |
| ½ inches (Midshaft) | 0.227 ± 0.002 | 0.223 ± 0.002 |
| 1 inches (Proximal) | 0.267 ± 0.005 | 0.242 ± 0.005* |
| Whole body (avg.) | 0.266 ± 0.003 | 0.252 ± 0.002* |

Significantly different from controls, P < 0.05 by a Dunnett's test for multiple comparisons.

Morphometric Study of cancellous bone (structural indices): Image analyses was done on digitized, two-dimensional images taken from the microradiographs of proximal tibial metaphyseal cancellous bone. Using an automated television microscope image analysis system (KSS Scientific Consultants, Magna, Utah) interfaced with a MacIntosh microcomputer, a 6.0 mm² cancellous bone area that enclosed the medial parts of the lateral and medial condylar medullary areas and central medullary area were quantified. The indices determined were the trabecular area (% area), perimeter to area ratio (mm/mm²), calculated trabecular thickness, trabecular number and trabecular separation. To describe the characteristics of trabecular structure and connectivity, "nodal" and "star volume" analyses was done as described for cancellous bone from the ovariectomized rat. Nodal analysis is a useful method to define the connectivity and structure of trabeculae from two-dimensional images. Using a nodal analysis program (KSS Scientific Consultants, Magna, Utah), the number of nodes and number and types of trabecular struts were determined from the microradiographic images of the same cancellous areas used for static morphometric analyses. The data collected included, the number and length of free to free, node-to-free and node-to-node struts. Marrow star volume is a direct measurement of trabecular separation and was determined using the same digitized cancellous bone image. The morphometric indices are provided in table 9. The trabecular bone area and number were significantly less in the OVX group than that of control. The thinner trabeculae in the OVX group, compared to controls, were indicated by the increased perimeter/area ratios in these groups and calculated trabecular thickness. The calculated trabecular separation was substantially increased in the OVX group compared with controls. The number of trabecular nodes and struts were substantially less in the OVX group compared with controls. The percentage of free-free struts was greater in the OVX group. But the percentage of node-free struts and node-node struts in OVX group were significantly less than that of controls. The average length of all the struts in OVX group was less than that in controls, but did not achieve statistical significance except in the length of node-node strut. It is believed that the absence of statistical significance is due to the number of animals tested and that statistical significance will be shown upon testing of a larger number of animals. The marrow star volumes were significantly greater in the OVX group compared with controls. These results revealed the relationship between cancellous bone structural changes and bone loss after ovariectomy.

TABLE 9

Static cancellous bone morphometry of proximal tibial metaphyses

|  | Control | Ovx |
|---|---|---|
| General parameters | | |
| Trabecular area % | 51.9 ± 4.0 | 20.2 ± 2.8* |
| Perimeter/area ratio (mm/mm$^2$) | 17.4 ± 1.6 | 31.2 ± 4.9* |
| Trabecular thickness, calculated (μm) | 91.5 ± 5.2 | 57.1 ± 7.2* |
| Trabecular number, calculated (No./mm) | 5.3 ± 0.2 | 3.5 ± 0.1* |
| Trabecular separation, calculated (μm) | 90.6 ± 6.1 | 228.4 ± 13.9* |
| Nodal analysis | | |
| Number of nodes | 133.5 ± 7.8 | 32.8 ± 2.6* |
| Number of struts | 210.3 ± 7.7 | 89.5 ± 6.3* |
| Type of strut (% of total) | | |
| Free-free | 1.4 ± 0.2 | 20.5 ± 3.3* |
| Node-free | 22.4 ± 4.7 | 52.0 ± 2.8* |
| Node-node | 76.2 ± 4.8 | 26.8 ± 4.8* |
| Average length of strut (μm) | | |
| Free-free | 134 ± 30 | 147 ± 11 |
| Node-free | 142 ± 4 | 146 ± 14 |
| Node-node | 178 ± 1 | 263 ± 28* |
| Star volume analysis: Marrow volume (mm3) | 0.04 ± 0.01 | 0.32 ± 0.08* |

Significantly different from controls, P < 0.05 by a Dunnett's test for multiple comparisons.

Histomorphometric study of the metaphyseal cancellous bone and endochondral growth rates: The histomorphometric measurement was performed on a 3 mm$^2$ area of the proximal tibial metaphyseal spongiosa. This area included both the lateral and central spongiosa regions of the primary and secondary spongiosa. This measurement was performed using a fluorescence microscope (Nikon, Tokyo, Japan) with a camera lucida attachment and a digitizing table interfaced with a microcomputer (Apple SE, Cupertino, Calif.) running histomorphometry software (KSS Scientific Consultants, Magna, Utah). The primary indices measured in this study included single labeled surface, double-labeled surface, total bone surface, interlabel width and osteoclast surface. The calculated indices included the mineralizing surface, surface referent bone formation and bone turnover rates. The mineral appositional rate was corrected for section obliquity. Endochondral growth (longitudinal growth) rates, expressed in μm/day, were determined by measuring the distance from the last fluorochrome label to bottom of the growth plate. The growth plate thickness, average hypertrophic cell size and the calculated rate of chondrocyte production per day were determined as previously described by Drs. Miller and Jee.[81] This data is listed in Table 10. In the OVX group, the proximal tibial growth plate was thicker compared with controls. Although the growth rate, hypertrophic cell size and calculated rate of cell production were larger in OVX group compared with controls, they did not achieve statistical significance. The double labeled surface, mineral appositional rate, surface referent bone formation rate, bone turnover rate and osteoclast surface were significantly increased in the cancellous bone of the proximal tibial metaphysis of OVX animals compared with controls. The mineralizing surface in OVX group was larger than that in controls, but did not show a statistically significant difference. Again, the absence of statistical difference is believe to be due to the number of animals used and that using a larger number of animals will improve the results of the statistical analyses. This study showed that ovariectomy results in significantly reducing cancellous bone mass and increasing bone formation, bone turnover rate and osteoclast surface likely due to the reduction in the suppressive effects of estrogen on bone turnover.

TABLE 10

Data of endochondral growth and cancellous bone morphometry:

|  | Control | Ovx |
|---|---|---|
| Endochondral growth | | |
| Growth rate (μm/d) | 17.4 ± 1.0 | 20.5 ± 0.9 |
| Growth plate thickness (μm) | 152 ± 4 | 177 ± 7* |
| Hypertrophic cell size (μm) | 14.9 ± 0.6 | 16.2 ± 1.2 |
| Calculated rate of cell production (cells/d) | 1.16 ± 0.06 | 1.37 ± 0.03 |
| Cancellous bone morphometry | | |
| Double labeled surface (%) | 14.3 ± 4.5 | 28.8 ± 2.9* |
| Mineralizing surface (%) | 22.2 ± 6.1 | 27.9 ± 5.0 |
| Corrected mineral appositional rate (μm/d) | 0.6 ± 0.04 | 1.3 ± 0.3* |
| Bone formation rate, surface referent (μm2/μm/d) | 0.088 ± 0.032 | 0.383 ± 0.106* |
| Bone turnover rate (%/Y) | 127.4 ± 58.6 | 382.4 ± 86.3* |
| Osteoclast surface (%) | 8.5 ± 1.5 | 27.4 ± 1.7* |

Significantly different from controls, P < 0.05 by a Dunnett's test for multiple comparisons.

It should be mentioned that several bone sites such as a growing cancellous bone site (proximal tibial metaphysis), a non-growing cancellous bone site (the distal tibial metaphysis) and the cortical bone site (the tibial shaft) may also be used for histomorphometric and morphometric analyses. Also, femoral, humeral and tibia bone, lumbar vertebral body and mandible are tested, as well as, multi-sections of each specimen. This provides data relevant to different bones and bone sites, which may have a different sensitivity to iron catalyzed oxidative damage and have altered responses to the treatments of the invention.

EXAMPLE VIII

The administration of an iron chelator (for example, an amphipathic polyaminocarboxylic acid chelator, GL22) and/or the administration of an established antioxidant, for example, vitamin E (VE), and/or the combinative treatment of chelator and VE. Under the hypothesis being tested, if the increased iron and iron catalyzed free radical damage indeed causes the onset of osteopenia, these treatments should mitigate the disease development.

In another experiment, the dosages of chelator and/or VE is administered at a dosage of about 30 μmol to about 50 μmol/kg (body weight) and about 150 IU/kg to about 200 IU/kg of diet, respectively.

At 14 and 7 days prior to necropsy, oxytetracycline-hydrochloride and calcein will be given by intraperitoneal injections to all animals as described in aim 1. These fluorochromes will be given as bone markers for histomorphometry in aim 3. At the same day of necropsy, whole body BMC/BMD (in vivo) will be measured by DXA. The experimental schedule is presented in table 12 below.

TABLE 12

Proceeding schedule for the experiment:

| Groups | (No. animals) | Weeks | | | | | |
|---|---|---|---|---|---|---|---|
| | | 50 | 51 | 52 | 63 | 64 | 65 |
| Basal Control | (12) | L1 | L2 | B, S | | | |
| Sham Control | (12) | | | B, SHA | L1 | L2 | B, S |
| OVX Control | (12) | | | B, VOX | L1 | L2 | B, S |
| OVX Estradiol | (12) | | | B, OVX | L1 | L2 | B, S |
| OVX Chelator | (12) | | | B, OVX | L1 | L2 | B, S |
| OVX Vitamin E | (12) | | | B, OVX | L1 | L2 | B, S |
| OVX Chelator/ Vitamin E | (12) | | | B, OVX | L1 | L2 | B, S |
| | | | | Start | | Treatment | End* |

L1: Label 1.
L2: Label 2.
B: BMD measurement.
S: Sacrifice.
SHA: Sham.
OVX: Ovariectomy.
*If necessary, treatment will be continued as described above.

Four groups of OVX animals will receive treatments of estradiol, chelator, VE and a combination of chelator and VE, respectively. 17b-estradiol in benzyl alcohol/corn oil solution ((5 vol:95 vol) is given to one OVX group by IP injection of 10 µg/kg body weight. The injections are performed three times a week. All other groups (one SHAM and four OVX groups) will receive the oil solution without estradiol by the same IP injection. Chelation treatment with 30 µmol/kg body weight of GL22 in saline solution (pH 7.5) is orally administered by intubation with a blunt-ended stainless steel needle three times a week. All other groups will receive the saline solution without chelator by the same manner. These approaches eliminate the effects of free solutions and physical handling on drug treated animals. The dosages used in this proposal are based on knowledge known to a person of ordinary skill in the art. Vitamin E (150 IU/kg of diet customermade by Harlan Teklad (Madison, Wis.) is given during the treatment. Except for the excess VE (increased from 109 IU to 150 IU/kg), the diet is the same standard diet as described herein and during the treatment, the excess VE diet is used to replace the standard diet. Bone tissues is collected and prepared as described herein, for example, in the histomorphometric assay and the measurements of BMC/BMD, EPR and GFAAS. Cu contents in bone is measured by GFAAS to determine the possibility of Cu-catalyzed free radical formation in bone. The serum ferritin concentration is tested using commercial kit (BioCheck, Inc. Burlingame, Calif.). This assay provides information about the relationship between serum ferritin, skeleton iron and osteopenia and the effect of treatment on serum ferritin concentration.

It is believed that the chelation treatment will reduce the iron levels measured by EPR and GFAAS as well as LLOFR levels detected by EPR in bone, thereby preventing bone loss in OVX rats (increased BMC/BMD). Unlike chelation treatment, the VE treatment will decrease the LLOFR levels, hence providing protection against loss of bone. It is believed that the combinative treatment may prevent the bone loss more effectively by removal of iron and inhibition of free radical damage at same time. Thus, the invention provides a medicament and method for the treatment of postmenopausal osteoporosis.

EXAMPLE IX

Nanoparticulate systems of iron chelators are prepared and their abilities of targeting the brain, removing redox active iron, and protecting iron-induced oxidative damage in an Alzheimer transgenic mouse model are tested. It is believed that iron chelator nanoparticle systems in chelation therapy provide a beneficial treatment for diseases, such as Alzheimer's Disease (AD), osteoporosis and other diseases. The use of nanoparticles as a targeting vehicle is believed to provide an iron chelation therapy for Alzheimer's disease (AD). Other neurodegenerative diseases, such as Parkinson's disease, Friedreich's ataxia, β-thalassemia, refractory anemias, as well as, other oxidative damage mediated diseases may also be treated. The use of iron chelator nanoparticle systems may be used to target desired organs in iron chelation therapy.

Oxidative stress may be a factor in the development of AD in humans [1-5]. Strong evidence shows that elevated Fe levels, and possibly elevated levels of other metals such as Al, Cu, Zn, etc., may catalyze free radical formation, which in turn may enhance neurodegeneration in AD. Therefore, iron chelators may have great therapeutic potential against AD by removing excess iron and/or other accumulated metals from the brain. However, further efforts have been frustrated by difficulties with chelator administration, especially, transport across the blood-brain barrier (BBB). To facilitate crossing the BBB, increasing lipophilicity of chelators may be applied, but such an increase may promote chelator toxicity. Moreover, the chelator lipophilicity dramatically decreases once the chelator complexes the metal inside the brain. Hence, the complex may not be able to leave the brain and, thus may become an additional toxic factor. Thus, the ideal chelators for therapy of AD should be able to enter the brain to chelate excess metal ions and then retain the ability to leave the brain after complexing with the metal.

Chelators covalently bond to nanoparticles may be used to remove iron from the brain and to protect against metal induced free radical formation. The chelator nanoparticle may be assayed in an Alzheimer transgenic mouse model.

The nanoparticle may serve as a vehicle for the chelator to target the brain, cross the BBB in the free form using low density lipoprotein (LDL) transport mechanisms, and once complexed with metals, exit the brain using the same mechanisms. More specifically, the nanoparticle transport system is believed to have the ability to transfer hexadentate iron chelators across the BBB. This is important as hexadentate iron chelators possess many advantages in chelation therapy.[51]

EXAMPLE X

Synthetic Methods for Hydroxypyridinone Iron Chelators with Functional Groups for Conjugation The iron chelators of the invention include, but are not limited to: 2-Alkyl-N-(2'-hydroxyethoxy)methyl-3-hydroxyl-4-pyridinone chelators, which were synthesized using established methods.[82] Briefly, 3-benzyloxyl-2-alkyl-4-pyridinone was synthesized as described by Dobbin et al.[83] with a minor modification. First, 2-alkyl-3-hydroxyl-4-pyranone and benzylchloride were refluxed in alkaline condition to protect the 3-hydroxyl group. Then, the substitution reaction of 3-benzyloxyl-2-alkyl-4-pyranone with aqueous ammonia reacted for 48 h. 3-benzyloxyl-2-alkyl-4-pyridinone were silylated in hexamethyldisilazane under refluxing for 2 h and then alkylated using trimethylsilyl trifluoromethanesulfonate as a catalyst with benzyloxyethoxymethylchloride which could be replaced by (2-acetoxyethoxy)methyl bromide. $SnCl_4$ could also be used as catalyst in the alkylation reaction, but resulted in separation difficulties and low yields. Both of the protection groups were removed simultaneously by hydrogenation under $H_2$/catalyst in aqueous ethanol or by $BBr_3$ in $CH_2Cl_2$ at 4° C. The new chelators were obtained in pure form after crystallization from a 1:1 solution of $CH_3Cl$/MeOH.

herein were also found to be more effective than DFO at removing iron from ferritin. The removal of iron from ferritin was determined by incubation of horse spleen ferritin with chelators 1a and 1b in Tris buffer (25 mM, pH 7.5, 37° C.) at a concentration of 0.47 mM, using DFO (0.19 mM) as a reference chelator similar to that described by Kontoghiorghes. The concentrations of the iron complex were measured spectrophotometrically from $\lambda_{max}$ values. The kinetics of iron release were investigated for a of period up to 72 h.

(2) The chelators of 2-alkyl-N-(2'-aminoethyl or 3'-amniopropyl)-3-hydroxyl-4-pyridinone were synthesized using the procedure as following (Scheme 2).

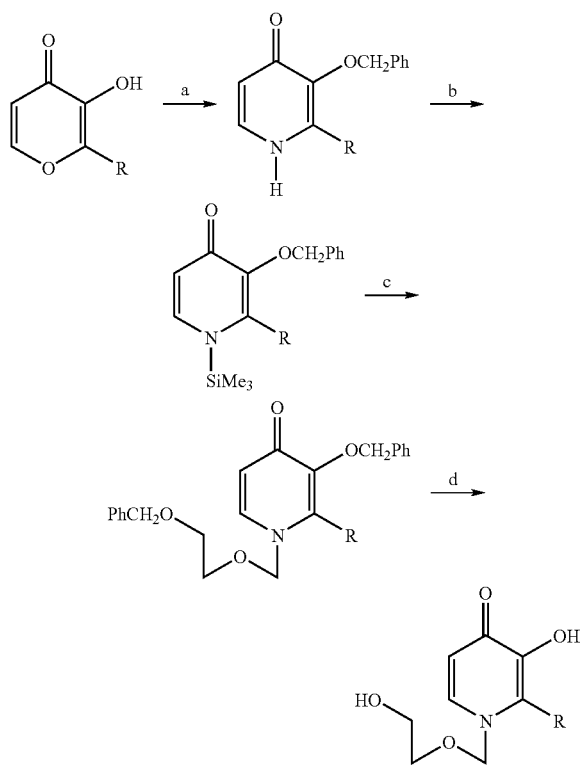

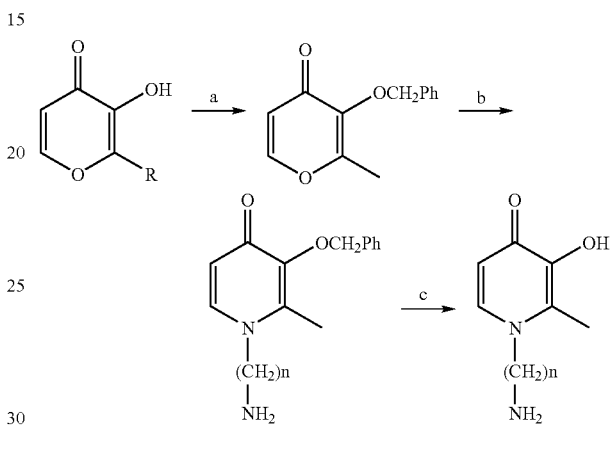

Scheme 2. R=Me, Et. a: benzylchloride/NaOH. b: $NH_2(CH_2)_2NH_2$ and $NH_2(CH_2)_3NH_2$/NaOH. c: $H_2$, Pd/C (or $BBr_3$ in $CH_2Cl_2$ at 4° C.).

In brief, 3-benzyloxy-2-methyl-4-pyrone was synthesized with benzylchloride in water and methanol (1:8 V/V) in the presence of NaOH and refluxed for 6 h. The product was then extracted 3 times with methylene chloride. It was reacted with 1,2-diaminoethane or 1,3-diamniopropane in 40% EtOH aqueous solution. After one week, the benzyl protective group was removed by $BBr_3$ in $CH_2Cl_2$ at 4° C. The final products were purified by crystallization using methanol and ether. The $^1H$-NMR chemical shift assignments in DMSO-$d_6$ are given as following. For n=2: 8.202 (1H, d, H-6), 7.153 (1H, d, H-5), 4.584 (2H, t, 1'-position ethylenic $CH_2$), 3.295 (2H, m, 2'-position ethylenic $CH_2$), 2.546 (3H, s, 2-position $CH_3$). For n=3: 8.214 (1H, d, H-6), 7.104 (1H, d, H-5), 4.407 (2H, t, 1'-position propylenic $CH_2$), 2.866 (2H, m, 3'-position propylenic $CH_2$), 2.516 (3H, s, 2-position $CH_3$), 2.021 (2H, m, 2'-position propylenic $CH_3$).

Scheme 1. R=Me (1a), Et (1b). a: benzylchloride/NaOH, then $NH_4OH$. b: hexamethyldisilazane, chlorotrimethylsilane. c: benzyloxyethoxymethylchloride, trimethylsilyl trifluoromethanesulfonate in 1,2-dichloroethane. d: $H_2$, Pd/C, in aqueous EtOH (or with $BBr_3$ in $CH_2Cl_2$ at 4° C.).

Characterizations have been done using proton-NMR, MS, UV-visible spectroscopy and elemental analysis. The molecular structure of chelator 1b was also confirmed by X-ray crystallography and the molecular structure is shown:

These chelators reacted with iron (III) forming purple complexes (UV: $\lambda$max=456 nm ($\epsilon 4.6 \times 10^3$) for 1a; $\lambda$max=459 nm ($\lambda 4.45 \times 10^3$) for 1b) which have the chelator iron stoichiometry of 3:1. This was demonstrated spectrophotometrically by titration of the chelators with iron in Tris buffer (25 mM, pH 7.5, 22° C.). The titration result reveals that the oxygens of hydroxyl and ether groups in the side chain did not involve the iron complexaton under physiological conditions. The chelators can also react with Al and Zn forming white powder complexes, and with Cu forming a green colored complex. These complexes were very soluble in water. A competition reaction between the new chelators and ferritin, an important storage protein for iron, demonstrated that the chelators can remove Fe from ferritin. Furthermore, the chelators described

EXAMPLE XII

The Alzheimer transgenic mice[84] is used as an animal model to evaluate chelation treatment, for example, an iron chelator nanoparticle, because increased redox active iron content has been found in the brain of this model. This replicates the findings in brain tissues of patients with AD.

Two bidentate and one hexadentate iron chelators are synthesized, then conjugated (also DFO) to at least one type of nanoparticle. In an exemplary embodiment, the nanoparticle has a diameter of about 300 nm. Hence, four chelator nanoparticle systems are formed with different surface properties. The formed systems are tested for metal binding capability by reactions with Fe, Al, Cu, and Zn. The plasma protein absorption pattern of the systems is assessed by 2D-PAGE, which provides information about the ApoE and ApoA-I absorption properties. Two chelator nanoparticle systems with better ApoE absorption before they are complexed with iron and with better ApoA-I absorption after they complex with iron are tested in the Alzheimer transgenic mice. Their ability to remove iron from the brain is determined by histochemistry and ICP-MS analyses. Protection from oxidative damage to the brain is determined by immunostaining. The chelator nanoparticle system may be optimized for use in the brain and for other iron overload diseases. This is believed to provide a beneficial use of nanoparticle technologies in therapeutic approaches to other diseases as well.

EXAMPLE XIII

The chelators to be conjugated with nanoparticles include, but are not limited to, bidentate chelators of 2-alkyl-1-(2'-hydroxyethoxy)-methyl-3-hydroxyl-4-pyridinone (1) and 1-(3'-aminopropyl)-2-alkyl-3-hydroxyl-4-pyridinone (2) and hexadentate chelators of N,N'-bis(2-hydroxybenzyl)-1-(4-aminobenzyl)-1,2-ethylenediamine-N,N'-diacetic acid (3) and 1,2-dimethyl-3-hydroxyl-4-pyridinone (L1), and DFO. The bidentate chelators are L1 derivatives that possess a functional side chain on the N-position that can be used for conjugation with nanoparticles (See scheme 3 and 4). Studies show that this type of side chain does not affect the iron binding ability. Therefore, the L1 derivative is likely to have high specific affinity to iron ($\log\beta=37$) and Al ($\log\beta=32$), and chelate Cu ($\log\beta=19.6$) and Zn ($\log\beta=13.5$) with an appreciable degree of efficiency. L1 virtually lacks affinity for calcium or magnesium chelation. Moreover, L1 derivatives are free charged in both free and complexing forms and the N-1 position side chain can be easily changed to optimize the chelator nanoparticle system, i.e., providing the functional groups to conjugate with other moieties and changing the lipophilicity/hydrophilicity. Different C-2 substituents may also influence the system-surface properties as well as iron binding, i.e., ethyl substituent increases the lipophilicity and the effectiveness of iron binding in vivo. Moreover, their toxicity due to lipophilicity may be limited after conjugation with nanoparticles. Hexadentate chelator 3 is a derivative of N,N'-bis(2-hydroxybenzyl)ethylenediamine-N,N'-diacetic acid (HBED). Chelator 3 possesses a linkage (4-aminobenzyl) that can conjugate with other molecules (Scheme 7). HBED is a synthetic hexadentate chelator with a very high affinity for iron ($\log\beta=40$) and little acute toxicity. It can also chelate Al ($\log\beta=25$), Cu ($\log\beta=21$), and Zn ($\log\beta=18$). Therefore, it can be used to simultaneously remove these metals in AD. HBED and its derivatives are widely used in laboratory research and clinic trials. However, their iron-removal capability after oral administration is much less efficient in the iron-overload-patient trials. HBED lacks the ability to cross the BBB due to its hydrophilicity and large molecular weight. While HBED has low toxicity in rats, significant CNS activity has been observed in the hypertransfused mouse model. Oral administration of HBED results in increased toxicity in which severe CNS inhibition and anorexia are observed. The use of the nanoparticle as a tool to deliver HBED offers the opportunity to increase the BBB penetration and limit the toxicity. DFO, as mentioned before, has already proved have some benefit for AD and the use of nanoparticles for delivery is used to improve its efficacy and resolve its toxicity. Because DFO contains an amino group, it can be easily conjugated to nanoparticles (Scheme 6). The linkers and surfactant coating influence the surface properties of chelator nanoparticle systems, which are factors for the in vivo organ distribution of the systems.

Chelator 2 can directly react with carboxylic acid functionalized nanoparticles preactivated by Sulfo-NHS(N-hydroxysulfosuccinimide) and CMC (N-cyclohexyl-N'-(2-morpholinoethyl)carbodimide methyl-p-toluensulfonate) (Scheme 5). The virtue of using Sulfo-NHS and CMC is that they are soluble in water and the converted Sulfo-NHS ester is more stable to hydrolysis and highly reactive only toward primary and secondary amines to form one amide bond. Each chelator before conjugation may be characterized spectroscopically using $^1$H-NMR, MS, UV-visible and IR.

The hexadentate iron chelator 3 is synthesized as published.[92] Because the chelator contains an active primary amine, it may be directly conjugated with carboxylic acid-functionalized nanoparticles (Scheme 6). The additional systems of the invention may be characterized by the same methods as described herein for the chelator nanoparticle systems or other methods known in the art.

For the purpose of bringing metal-chelator complexes out of the brain by nanoparticles, it is preferable to avoid the use of degradable polyisobutylcyanoacrylate particles. Instead, polystyrene nanoparticles are used, since it occurs in nature and is nontoxic. It is also commercially available with many different sizes and functional surfaces. Other modified polystyrene or other polymeric nanoparticles may also be used according to the invention. The sizes of the nanoparticles used for targeting of peptides to the brain includes, but is not limited to, rather large particles, ranging from about 10 to about 1000 nm. It is believed that the particle size may affect the brain targeting and uptake. Therefore, particles with size of about 300 nm are used in an exemplary embodiment. Other sizes of the particles are also included within the scope of the invention.

Two-dimensional polyacrylamide gel electrophoresis (2-D PAGE gel) analysis of the chelator-nanoparticle system after incubation in citrate plasma is used to determine the protein absorption pattern. The same analysis of the metal-chelator-nanoparticle system is also done. These assays provide information about adsorbtion of ApoE, passage through the BBB, and target the brain. It also determines absorption of ApoA-I after chelating metals, which increases the efficiency of the chelator nanoparticle's leaving of the brain. This information is also used to optimize improvements in chelators, linkages, surfactants and other characteristics.

Some of the preferred embodiments have the better ApoE absorption in the free form to facility entry into the brain and have the better ApoA-I absorption after complexing with iron to facility their leaving the brain.

The effect of the chelator nanoparticle systems in the treatment of AD are tested in the Azlheimer mouse model. This type of mouse has been shown to have increased A$\beta$ deposits, redox active iron content, and an array of oxidative markers such as heme oxygenase (HO-1), hydroxynonenal (HNE) and Pentosidine. This is similar to the types of oxidative damage found in Alzheimer's disease. Additionally, these mice can serve as a good animal model of Alzheimer's disease for testing iron removal and changes in iron induced oxidative damage caused by iron chelation therapy. Indeed, these mice have been used to test the removal of Cu and Zn by their chelators. The ability of chelator nanoparticle systems to remove iron from the brain and protection of oxidative damage are measured.[85] Moreover, some other metals (Al, Cu, Zn) are also measured simultaneously by using ICP-MS. The increased levels of these metals are suspected in the etiology of AD. Unconjugated DFO and nanoparticles without conjugated chelator are used as controls in the mouse system.

EXAMPLE XIV

Analytical- or higher-grade chemical reagents were purchased from Aldrich-Sigma and were used without further purification. Melting points of chelators were measured on a Fisher Johns apparatus without correction. 1H-NMR spectra were recorded at 200 Mhz with an IBM NR 200 spectrometer and UV-visible spectra on a Beckman DU-60. A Beckman Coufter Multisizer II was used to characterize microsphere particles. Elemental analyses were performed by Desert Analytic Organic Microanalysis Inc (Tucson, Ariz.).

The chelator 2-methyl-N-(3'-aminopropyl)-3-hydroxyl-4-pyridinone (MAHP) was synthesized using a modification of a procedure known in the art. In brief, 3-hydroxyl-2-methyl-4-pyranone (44.4 g, 0.352 mol) and benzyl chloride (51 g, 0.403 mol) were mixed in a solution of water (50 ml) and methanol (400 ml) in the presence of NaOH (15 g). The mixture was refluxed for 6 h with magnetic stirring. After removing methanol under vacuum, 70 ml of water were added and 3-benzyloxy-2-methyl-4-pyranone was extracted 3 times with 60 ml portions of methylene chloride. The combined methylene chloride was washed with 5% NaOH aqueous solution (50 ml), followed by water (50 ml) and dried over $MgSO_4$. The product was obtained after evaporation of the solvent under vacuum (94% yield). The product (4.41 g, 0.019 mol) was then reacted with 1,3-diaminopropane (1.15 g, 0.019 mol) in aqueous ethanol solution (30 ml water and 20 ml ethanol) at room temperature. After one week, solvents and residual diamine were evaporated under vacuum and the residue was dissolved in chloroform, washed 3 times with water and dried using $Na_2SO_4$. After removing the chloroform, methanol was added and the pH adjusted to 1 with HCl. The 1-(3'-aminopropyl)-3-benzyloxy-2-methyl-4-pyridinone was precipitated as dihydrochloride salt and collected by filtration. The pure product was obtained by crystallization from methanol and ether (yield: 80%) and the product (2 g, 0.0058 mol) further reacted with $BBr_3$ (30 ml, 1.0 M solution of $CH_2Cl_2$) in 120 ml of $CH_2Cl_2$. The mixture was stirred overnight at room temperature under a nitrogen atmosphere. Then, 160 ml of water was added and stirring was continued for an additional 4 h. The aqueous phase containing the MAHP was separated and evaporated under vacuum. The crude MAHP was purified through crystallization twice using ethanol and ether (96% yield). Pure MAHP was identified by $^1$H-NMR and elemental analysis. $^1$H-NMR (DMSO-d6): 8.214 (1H, d, H-6), 7.104 (1H, d, H-5), 4.407 (2H, t, 1'-position propylenic $CH_2$), 2.866 (2H, m, 3'-position propylenic $CH_2$), 2.516 (3H, s, 2-position $CH_3$), 2.021 (2H, m, 2'-position propylenic $CH_3$).

Elemental analysis: Calcd. For $C_9H_{14}N_2O_2$ 2HBr C, 31.42; H, 4.69; N, 8.14. Found: 31.52; H, 4.79; N, 7.75, m.p.: 242° C.

Figure 7A:
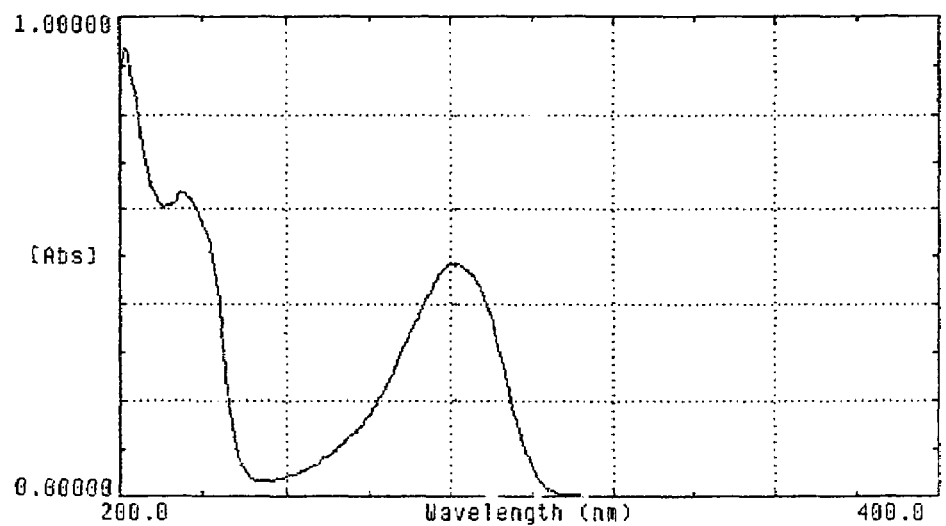
FIG. 7A illustrates the UV-visible absorption of free MAHP ($\lambda max=281$ nm, $\epsilon=1.43\times10^4$) and 7B illustrates the absorption of iron-MAHP complexes ($\lambda max=455$ nm, $\epsilon=3.02\times10^3$).
Figure 7B:
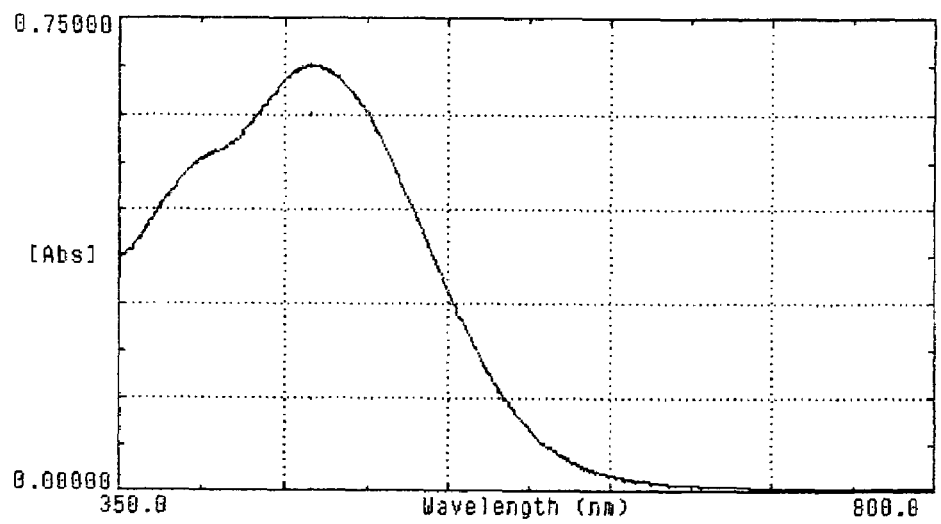

Conjugation of MA PH and DFO with Magnetic Microsphere Particles:

Monodispersity polystyrene microsphere particles with sealed magnetite inside (2.8 μm diameter, 30 mg per ml, 150 micromole carboxyl groups per gm, Dynal, Inc., Lake Success, N.Y.) were used. The carboxylic acid functional groups on the particles surfaces were pre-activated by CMC (N-cyclohexyl-N'-(2-morpholinoethyl)carbodiimide methyl-p-toluensuffonate) and conjugated with MAHP or DFO.[89,90] Briefly, the carboxylated particles were re-suspended through pipetting and vortexing. Then, 0.5 ml of 15 mg particles (approximately 2.3 micromole of carboxylic groups) was immediately transferred into a 1.5 ml micro-centrifuge tube and the supernatant removed by magnetic separation with a magnetic particle concentrator (MPC, Dynal, Inc., Lake Success, N.Y.). The particles were suspended in 0.5 ml of 0.01 M NaOH, mixed well for 5 min. and the process was repeated. Particles were washed twice with 0.5 ml of 0.1 M MES (2-[Nmorpholino] ethane sulfonic acid) buffer (pH 5.0) and once with 0.3 ml of cold Milli-Q water. Carboxyl groups on the particles were activated by adding 0.5 ml of cold Milli-Q water containing CMC (0.01 M) and incubating for 10 mm at 4° C. with slow tilt rotation. After removal of the supernatant by magnetic separation, 0.4 ml of CMC solution was added again along with 0.2 ml of 0.3 M MES buffer (pH 5.0). The mixture was vortexed and incubated as above for 30 min. The particles with activated carboxyl groups were washed twice with cold 0.1 M MES as quickly as possible and re-suspended in 0.5 ml of 0.1 M MES buffer (pH 5.0) containing excess MAHP (0.01 M). The mixture was vortexed, followed by incubation for 30 min. at room temperature with tilt rotation. The particles conjugated with MAHP were washed with 0.1 M MES buffer twice and PBS (phosphate buffered saline, pH 7.4) twice more (4×0.5 ml) and stored in 0.5 ml of PBS at 4° C. The yield of conjugation was determined by measurements of the free chelator concentrations in the solution before and after conjugation using UV-visible spectrometer at the wavelength of maximum absorption (281 nm, $\epsilon 1.43\times 10^4$) (FIG. 7A). The difference in measurements showed that the degree of the coupling was about 68% based on the carboxyl groups on the particles. The concentration and size distribution of the MAHP-particle systems was determined using a Beckman Coulter Multisizer II in a counting cuvette containing Isoton II diluent (Beckman Coulter, Inc., Miami, Fla.). The identical procedure was employed to conjugate DFD with particles.

Reaction of MAHP- or DFO-Microsphere Systems with Ferric Iron:

A 0.5 ml aliquot of freshly-prepared ferric iron solution ($Fe(NO_3)_3$, 0.002 M) in MES buffer (0.01 M, pH 5.0) was added to 0.1 ml of MES (0.01 M, pH 5.0) solution containing the suspended MAHP-particle system (3 mg). The mixture was rotated at room temperature for 4 h. The iron-MAHP-particle system and supernatant were separated using a magnetic particle concentrator. The systems were thoroughly washed with MES buffer 5 times to remove noncomplexed iron ions. After combining the supernatants, excess MAHP in MES buffer (1 ml, 0.01 M) was added to complex the iron ions that did not react with the MAHP-particle system. The visible absorbance of the iron-MAHP complex was measured using UV-visible spectrophotometer at a maximum wavelength of 455 nm ($\epsilon 3.02\times 10^3$) after the chelating reaction reached equilibrium. A standard curve for iron concentration was obtained by measuring several solutions of iron-MAHP complex with known iron concentrations. The identical procedure was applied to the investigation of the reaction of the DFO-particle system with ferric iron.

MAHP was synthesized according to the published literature protocol[91] with some modifications that improved production yields. For the reaction of 3-benzyloxy-2-methyl-4-pyranone with 1,3-diaminopropane (Step b in Scheme 1), reflux incubation time was modified from 18 h to one week at room temperature. Additionally, for the removal of the benzyl protective group (Step c in Scheme 1), $BBr_3$ was used to produce the hydrogenolysis reaction rather than $H_2$-Pd/C. Under this particular modification, the total yield of the two-step reaction was increased to 77%, compared to 68% obtained in the original reaction. The final MAHP from this modification was in the form of a dihydrobromide salt instead of dihydrochloride, as reported in literature.[91]

MAHP is a derivative of L1 where the methyl group on the nitrogen atom at position 1 is replaced by a 3-aminopropyl-side chain. According to X-ray structural analyses this type of replacement has little effect on the geometry of the iron-binding site, thus the affinity for iron remains unchanged. The formation of a complex between iron and MAHP was indicated by a color change of the ESM buffer solution; colorless with free MAHP and turning orange once ferric iron was added to the MAHP buffer solution. The wavelength of maximum absorption at 281 nm ($\epsilon 1.43 \times 10^4$) was observed for free MAHP (FIG. 8A), whereas the wavelength of maximum absorption at 455 nm ($\epsilon 3.02 \times 10^3$) was used for iron-MAHP complexes (FIG. 8B). Changing different side chains in L1 provides a way to optimize such pharmacological properties as lipophilicity/hydrophilicity and chelation efficacy. Additionally, if these side chains contain functional groups, the active sites can be used for further modifications. In these examples, both MAHP and DFO had a primary amino group in their side chains, thus providing a functional group for microsphere particle conjugation.

Some magnetic microspheres, such as Dynal magnetic particles, are commercially available. These beads are prepared with functional groups on their surface for the purpose of conjugation and have shown the ability to conjugate nickel chelators for protein purification. Here, the same type of particle has been used to demonstrate the conjugation of iron chelators and the iron binding capability of the chelator-particle system. The particles were composed of cross-linked polystyrene with superparamagnetic material that was magnetic only when placed in a magnetic field. The magnetite was sealed in pores of the particles and chelatable iron was not observed in the particles. This was demonstrated by a lack of evidence for iron-MAHP complex formation monitored by UV-visible spectrophotometer readings after an overnight incubation of the particles with MAHP in a MES buffer solution at room temperature. Their mono-dispersity, sphere shape and constant surface area limited non-specific absorption and chemical agglutination observed with irregular particles. On the surface of the microsphere particles, there were carboxylic acid functional groups (approximately 150 micromol per gram) that allowed the microsphere particles to conjugate to MAHP or DFO by forming a covalent amido bond. Prior to conjugation, the carboxylic acid groups were first activated through carbodiimide in MES buffer at an acidic pH 5 to form an active intermediate of the ester (Scheme 2). To remove excess carbodiimide, the beads were rapidly washed with cool Mill-Q water since the ester was unstable and underwent hydrolysis. An alternative method, such as adding a water-soluble N-hydroxyl compound like sulfo-N-hydroxysuccinimide (NHS), may increase the coupling yield, since NHS form a more stable intermediate of the ester by replacing the Oacylisourea intermediate formed by carbodiimide. The NHS-formed ester is less susceptible to hydrolysis but still highly reactive toward amino groups. The primary amino group in the chelators used in this study reacted with active ester intermediates derived from carboxyl groups on the particle surfaces and formed covalent amido bond linkages in good quality yields (Scheme 2).

Figure 9:
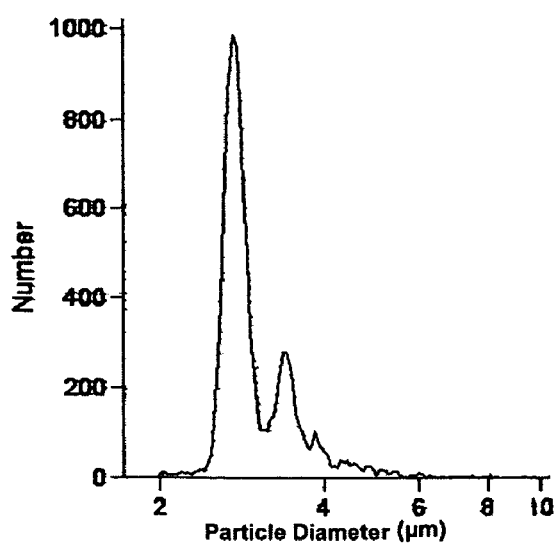
FIG. 9 illustrates the particle-size distributions measured by a Multizer Analizer II. There is no distribution change between particles conjugated with MAHP and particles without conjugation.

Coupling yields were easily determined by (1) measuring the free chelator concentration in solution before and after conjugation, using UV-visible spectrophotometer readings to determine the absorbance of MAHP at 281 nm, and (2) calculating the difference between the two concentrations that indicates the amount of chelator conjugated to microsphere particles. After the conjugation reaction, the particle size distribution was measured and compared with the distribution prior to conjugation using a Multizer analyzer II. A distribution change was not observed, an indication of no particle clumping after chelator conjugation (see, FIG. 9).

As will be recognized by a person of ordinary skill in the art, conjugation of the chelators with nano- and micro-particles is not limited to the use of amido bonds. A variety of covalent bonds, including, but not limited to, amine and ether bonds, may be formed, depending on the existing functional groups located on the chelator and/or the particles.

Figure 8:
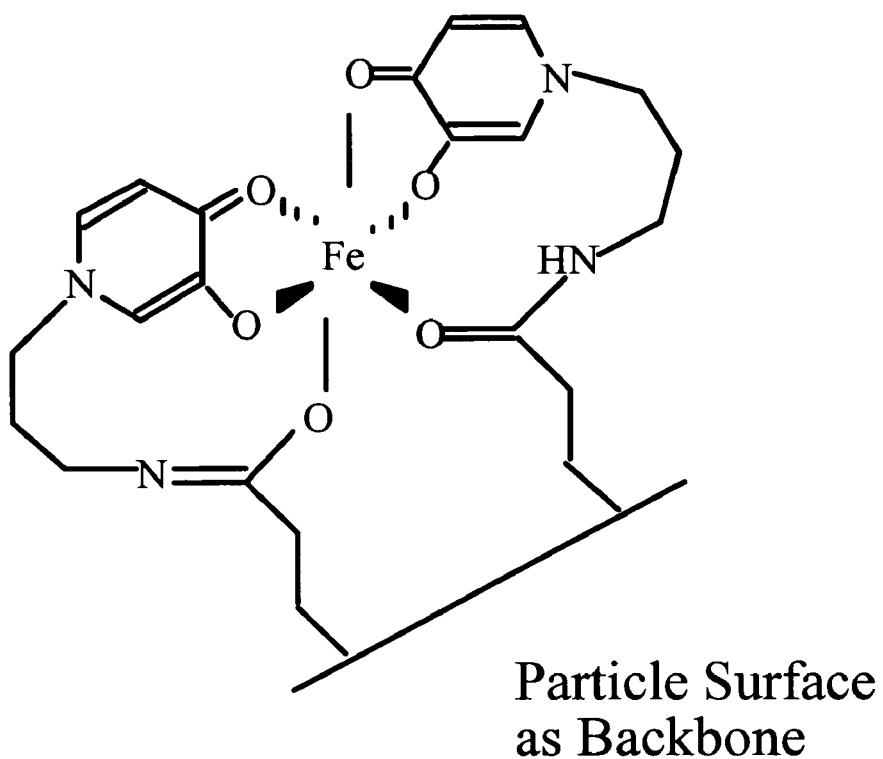
FIG. 8 shows four oxygen donors for two MAHPs and two oxygen donors from amido groups constructing a hexadentate chelator through particles surfaces as the backbones.

The ability of the chelator-particle systems to complex iron was tested by incubating the systems with a $Fe(NO_3)_3$ solution. After the reaction was complete, the $Fe(NO_3)_3$ solution was removed and non-complexed iron was determined by adding MAHP and subsequently measuring the iron-MAHP complexes using UV-visible spectroscopy. Results indicate that about two MAHP molecules complexed with every one-iron atom. Because each MAHP can provide only two oxygen donors to chelate iron, two more iron-binding sites are needed to form a highly stable complex with an octahedral coordination sphere. Since the oxygen atoms in amido groups may be involved in chelating iron, two oxygen donors from two amido groups and four oxygen donors from two MAHPs are believed to assemble into a hexadentate chelator, using microsphere surface linkages as the backbone (FIG. 8). This is significant, as hexadentate iron chelators possess many advantages including kinetic stability, concentration independence of iron affinity, and low toxicity. In addition, attempts to convert bi- or tridentate iron chelators into hexadentate chelators with various backbones suffer mainly from decreased bioavailability and the risk of potential toxicity. In contrast, the use of microsphere particles to convert bi- or tridentate chelators to hexadentate chelators may not possess these problems, for example, due to the particle targeting ability. In this manner, many bidentate or tridentate iron chelators, even with intolerable toxicity due to lipophilicity, may be modified by conjugation with nano- or micro-particles, since the lipophilic character of the chelators no longer contributes to the toxicity. These results also reveal that DFO still retains the 1:1 complex ratio with iron, an indication that conjugation with particles does not affect iron binding ability. The invention also demonstrates that the bioavailability of some hexadentate iron chelators with high molecular weights and hydrophilicity can be improved after formation of the chelator-particle delivery system.

EXAMPLE XV

Determining the protein absorption pattern of the new systems before and after metal chelating by using 2-D PAGE gel analysis: Plasma protein absorption pattern on nanoparticles is believed to be a key factor for the systems in vivo organ distribution and 2-D PAGE may be used for the analysis of adsorbed proteins on nanoparticles. Therefore, 2-D PAGE gel analysis of the chelator-nanoparticle systems after incubation in citrate plasma is used to determine the protein absorption pattern. The same analysis of metal-chelator-nanoparticle systems is done.

Determining the abilities of chelator nanoparticle systems to remove iron and to protect oxidative damage in the brain of Alzheimer transgenic mice: Sixty 23-month old Alzheimer transgenic mice, FVBXC57B6/SJL are obtained from the Alzheimer's Disease Research Center at Case Western Reserve University, given two months to acclimate to local vivarium conditions (22° C. and 12 h/12 h light-dark cycle) and fed ad libitum. During the study, the mice are weighed at intervals and abnormalities such as ruffled fur, lethargy, tremor are monitored. At the age of 25 months, the oxidative markers and redox active iron are robustly displayed in the brain of the Alzheimer transgenic mice compared to control mice. The mice are divided into five groups (twelve each).

cator on polyester plate. Elemental analyses performed by Desert Analytic Organic Microanalysis Inc. (Tucson, Ariz.).

Synthesis of iron chelator-nanoparticle systems: The general synthesis of the chelator 1 is described in scheme 3.[86]

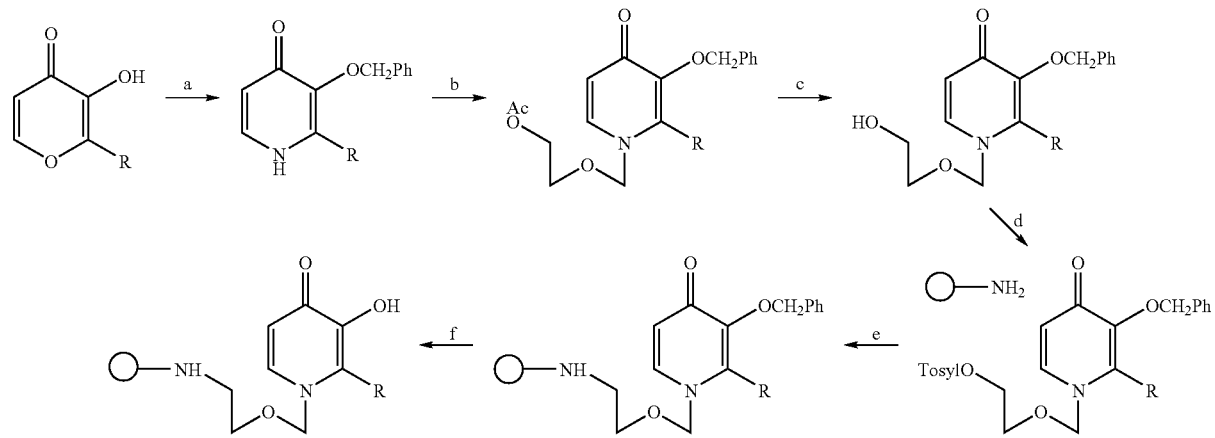

25

Two groups are injected with two different chelator nanoparticle systems in saline, respectively. The remaining three groups will serve as the controls; one injected with DFO in saline, another just with nanoparticles in saline, and the last one just with saline. The compounds are given by tail vein injection, 3 times a week. The treatments are continued for 2 months. In each injection, about 1.5 µmol bidentate iron chelator with nanoparticles in 0.1 mL saline or 0.5 µmol hexadentate chelator with nanoparticles in 0.1 mL saline for each 10 g body weight of mouse are used. The brain tissue is obtained after decapitation of the mice. Following perfusion by saline, six intact brains from each group are fixed in methacarn for redox active iron and oxidative marker measurements by histochemistry and immunostaining. The other six are weighed and snap frozen in liquid nitrogen for total iron measurement as well as some other metals, i.e., Al, Cu, Zn by ICP-MS. The details of experimental methods can be found in the references and are described herein.

EXAMPLE XVI

Materials

Chemicals and biochemicals will be of analytical grade or better from Aldrich and Sigma (St. Louis, Mo.). Nanoparticles with amino or carboxylic acid functionalized surfaces are obtained from Bangs Laboratories, Inc. (Fisher, Ind.). Melting points of newly synthesized chelators are determined on a Fisher-Johns melting point apparatus without correction. $^1$H-NMR spectra are recorded at 200 MHz with an IBM NR 200 spectrometer. The analysis of mass spectrometry are performed by the shared research facilities at the University of Utah or Galbraith Laboratories, Inc. Knoxville, Tenn. IR spectra are recorded, as KBr discs, using a beckman 2100 spectrometer. UV-visible spectra are recorded on a Beckman DU-64. Atomic absorption spectra are obtained using a Perkin-Elmer 3100 atomic absorption spectrophotometer. A Model 6000A HPLC (Water Associates) are used for testing of chelator purity and chelaor nanoparticle coupling degree. Column chromatography is performed with Aldrich silica gel (70-230 mesh). Thin layer chromatography (TLC) is done on Sigma acid-washed silica gel with a 254 nm fluorescent indi- Scheme 3. R=Me, Et. a: benzylchloride/NaOH/. b: $NH_4OH$. C: hexamethyldisilazane/chlorotrimethylsilane/(2-acetoxyethoxy)methyl bromide, trimethylsilyl trifluoromethanesulfonate in 1,2-dichloroethane. c: basic hydrolysis with $NH_4OH$. d: tosyl chloride in pyridine. e: nanoparticles with amino functional groups. f: $BBr_3/CH_2Cl_2$ at 4° C. for 30 min.

Instead of benzyloxyethoxymethylchloride, 2-acetoxyethoxy)methyl bromide is used and the synthetic method is the same as described herein. The acetyl protection group on the side chain is removed by basic hydrolysis in methanolic ammonia solution. The mixture is stirred at room temperature in a sealed flask for 24 h. After purification by silica gel chromatography using $CHCl_3$-MeOH (8:1) as an eluent, the deprotected hydroxyl group is converted into P-toluene-sulphonyl (tosyl) ester by the reaction with tosyl chloride (1.1 moles per mole of chelator) in dry pyridine. After removal of the solvent, the crude ester is often used directly. Before conjugation, 1 mL (100 mg/mL) of amino-modified nanoparticles are washed in 10 mL of 0.1 M sodium phosphate buffer (pH 7.4). After second wash, resuspend pellet in 10 mL of tosyl activeted chelator solution, ensuring that the particles are completely suspended by vortexing. Allow to react at 37° C. for 24 hours with continuous mixing. Separate the particles conjugated with chelators by centrifugation and wash with phosphate buffered saline (pH 7.4) four times. Then, deprotect OH on pyridinone ring by $BBr_3$ in $CH_2Cl_2$ at 4° C. with shaking for 30 min. The new chelator-particle system is obtained by centrifugation and wash four times with PBS buffer. Resuspend in 10 mL 25 mM Tris buffer (pH 7.4) and store at 4° C. until used. As mentioned above, if the nanoparticles could be damaged during the deprotective step, we will use an altered method to conjugate the chelator. The toluene sulfonic group (Tosyl-O-group) may be changed into an amino group by nucleophilic displacement reaction. To obtain primary amines in reasonable yield, sufficient excess ammonia is used. After that, first, deprotection of the OH group on the pyridinone ring by using the same deprotective method as above, then conjugate the chelator to Sulfo-NHS (N-hydroxysulfosuccinimide) preactivited carboxylic acid functinal nanoparticles just like chelators 2, 3, and DFO do.

The chelator concentrations of the reaction solution before and after conjugation are determined by using UV-visible spectroscopy or HPLC, thereby the amount of the chelator conjugated to nanoparticles can be obtained by simply multiplying the difference of the concentrations with the reaction volume.

Chelator 2 may be synthesized as described herein and as known in the art. (scheme 4).

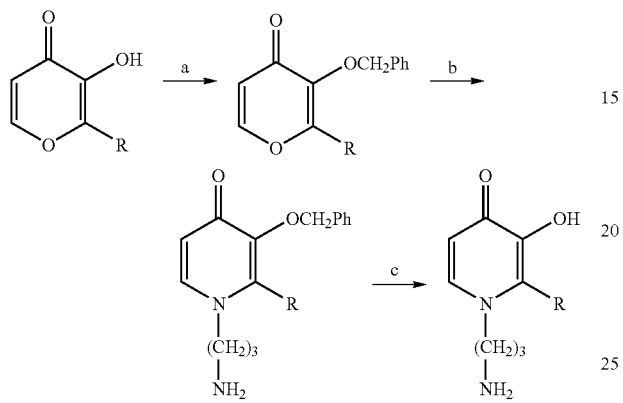

Chelator 2 can react with carboxylic acid functionalized nanoparticles preactivated by Sulfo-NHS, which are prepared as follows. The nanoparticles with carboxylic acid surface functional groups are resuspended by pipetting and vortexing. Immediately pipette 100 µL into a 1.5 mL Eppendorf tube and remove the supernatant by centrifugation. Resuspend beads in 100 µL of 0.01 M NaOH. Mix well for 5 min. and repeat. Wash beads twice with 100 µL of 0.1 M MES (2-[N-morpholino]ethane sulfonic acid) buffer pH 5.0 and once 100 µL of cold Milli-Q water. Resuspend the particles with 200 µL of 0.3 M MES (0° C.) containing Sulfo-NHS and add dropwise 50 µL of 0.02M CMC in cool Milli-Q water. Vortex and incubate for 2 h at 0° C. with slow tilt rotation. Add acetic acid (5 µl) to quench the reaction and incubate for another 1 h at 0° C. Remove supernatant by centrifugation. Wash particles twice with cold 200 µl of 0.1 M MES as quickly as possible. Resuspend nanoparticles in 200 µL of PBS buffer containing excess chelator 2. Vortex to ensure good mixing. Incubate for 30 min at room temperature with slow tilt rotation. Wash with 200 µL of PBS four times. Resuspend nanoparticles in 200 µL of PBS and store at 4° C. (Scheme 5 and 6).

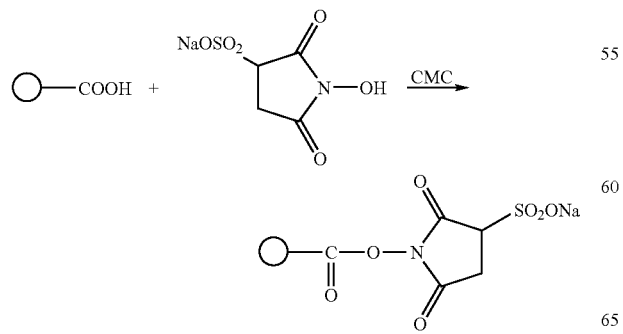

Scheme 5. Activizing COOH on nanoparticles by Sulfo-NHS and CMC:

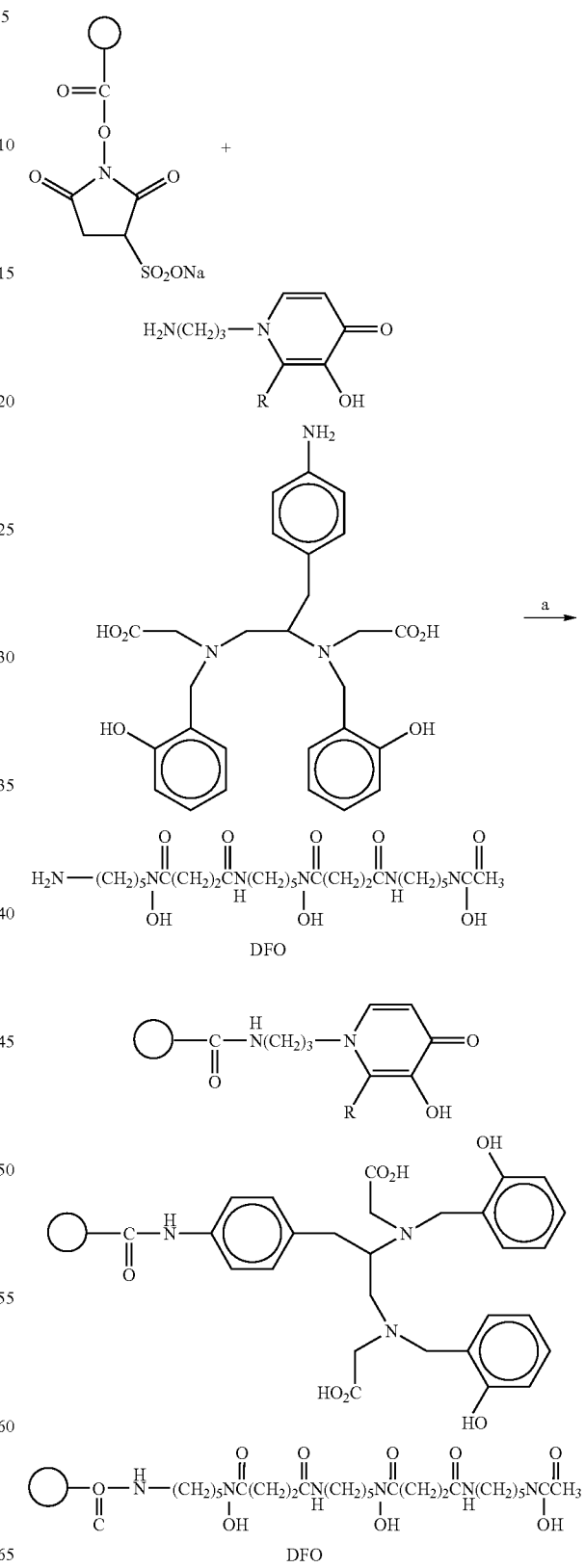

Scheme 6. a: conjugation in PBS at room temperature for 30 min.

Hexadentate chelator 3 is synthesized according to reference. Briefly, 1-(4-Nitrobenzyl)ethylenediamine and salicylaldehyde are heated at 80° C. for 20 min in absolute ethanol. The formed Schiff base is reduced by NaBH4 in absolute ethanol and ethylene glycol dimethyl ether at room temperature for 2 h. The reduced Schiff base is heated with bis(trimethylsily)acetamide (BSA) at 60° C. for 2 h and then at 90° C. for 1 h. After standing at room temperature for 16 h, remove BSA and add dry benzene, trimethylsilyl bromoacetate, and 2,4,6-collidine. Heat the mixture at 40° C. for 5 h and stand at RT for 15 h. After removal of liquid under vacuum, add 6N HCl and stir the mixture at room temperature for 15 h. Product is isolated by extraction of byproducts using ethyl ether. The nitro group is reduced by hydrogenation with 10% Pd/C at 0° C. for 5 h. The synthesis is carried out as shown in scheme 7.

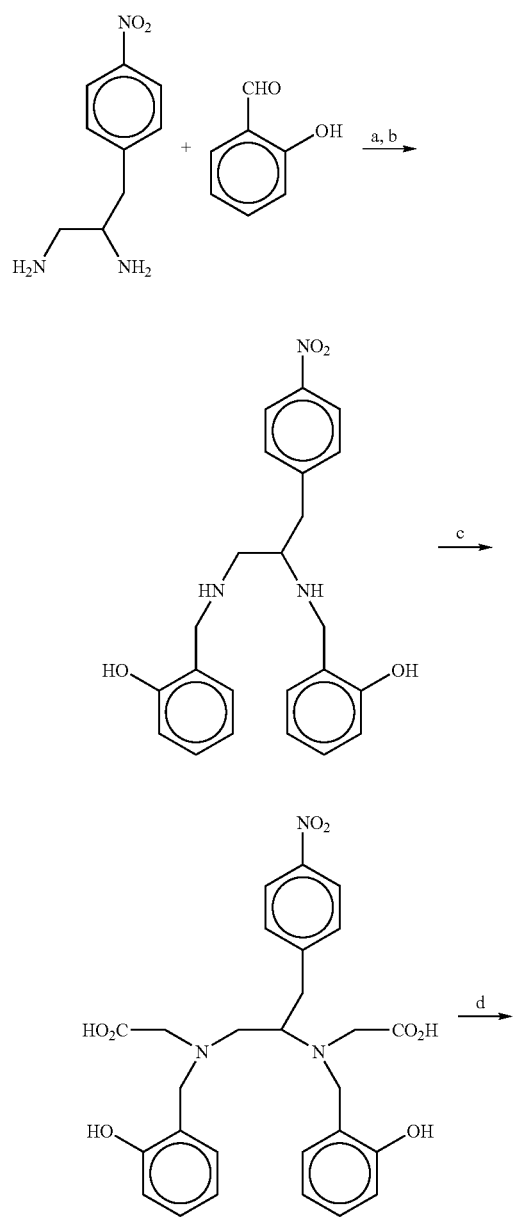

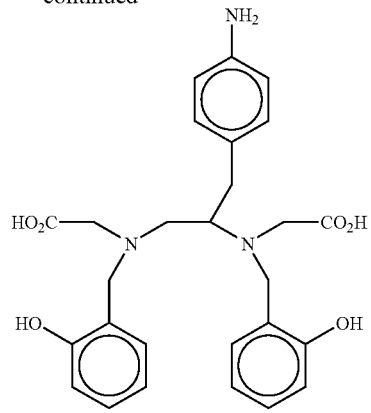

Scheme 7. a: 80° C., 20 min in EtOH. b: NaBH4 in EtOH/ethylene glycol dimethyl ether, room temperature, 2 h. c: BSA/trimethylsilyl bromoacetate/2,4,6-collidine. d: $H_2$, 10% Pd/C at 0° C. for 5 h.

Conjugate the chelator 3 and DFO directly with Sulfo-NHS-preactivized-carboxylic acid functionalized nanoparticles are prepared as for chelator 2 (Scheme 6).

EXAMPLE XVII

The ability of the chelator-nanoparticle systems to chelate Fe, Al, Cu, and Zn is determined by atomic absorption spectroscopy. The chelator-particle systems are added to fresh prepared metal salts in Tris buffer solution (pH 7.4) and the mixture is shaken at room temperature for 20 min. Separation of the system is done by centrifugation and washing the systems four times with Tris buffer. The chelators are decomposed by adding 3N $HNO_3$ and incubate at 60° C. for 2 h with shaking, then measuring the metal ions by atomic absorption spectroscopy. The standard curve is made by the mixture of nanoparticles and several different known concentrations of metal-chelator complexes and decomposition in the same condition as above.

2-D PAGE gel analysis of the chelator-nanoparticle system after incubation in citrate plasma is used to determine the protein absorption pattern. The same analysis of the metal-chelator-nanoparticle system is also done. Human blood is collected in an Evacuated tube containing Sodium citrate as anticoagulant from a healthy, adult volunteer. After centrifugation, the separated plasma is frozen at −20° C. and stored for later use. 200 μL of each system (2.5% W/V) is incubated in 2.2 mL of citrate-stabilized human plasma for 5 min at 37° C. After separation by centrifugation and washing four times with Milli-Q water, the adsorbed proteins is eluted from the surface by a protein solubilizing solution and applied to the 2-D PAGE. In the first dimension, isoelectric focusing, the proteins are separated according to their isoelectric points (pI). In the second dimension, SDS-PAGE, the separation is based on the different molecular weight (MW) of the proteins. After SDS-PAGE the gels are silver-stained, and scanned with a laser densitometer. The gel images are analyzed and edited using MELANIE II software (Apple91). As each protein from human plasma appearing on a gel has its own well defined coordinates (pI and MW), proteins can be identified by matching the gels obtained to the 2-D reference map of human proteins. While the data is regarded as only semiquantitative, it may be used for a reliable approximation of the amount of protein adsorbed.

The chelator nanoparticle systems in saline (1.5 μmole of bidentate chelator or 0.5 μmole of hexadentate/0.1 mL saline for each 10 g body wt) is intravenously injected through the tail vein. In the same manner, 0.5 μmole of DFO in 0.1 mL saline, nanoparticles with the average of the amounts of the two chelator nanoparticle systems used above in 0.1 mL saline, and 0.1 mL saline only for each 10 g body wt is given to the three control groups, respectively. Restraining tubes and needles with external diameter of 0.4 mm or less is used. The needle used is cut into two halves with a polyethylene tubing mounted in-between. Injection is carried out slowly and air must be removed from the needle and syringe before injection. Warming the tails of the mice in 45° C. water or the whole body under a heating lamp may be used to dilate the tail veins. The injection is given 3 times a week and the treatment is continued for 2 months. The mice are weighed at intervals and observed for toxicity [20].

The mice are killed by decapitation and the brains are quickly obtained on ice. Following perfusion by saline, six intact brains from each group are fixed in methacarn (methanol/chloroform/acetic acid, 6:3; 1 by volume) for histochemical and immunochemical detection. The other six brains are weighed and snap frozen in liquid nitrogen for total iron measurement by ICP-MS. After 16 h of fixing, the tissue is dehydrated through graded ethanol followed by xylene and embedded in paraffin. Six-micron-thick sagittal sections through the entire brain, including all cortical regions and the cerebellum, are cut and mounted on Silane-coated glass slides (Sigma). For iron histochemical detection, sections are deparaffinized with xylene and rehydrated through graded ethanol, then incubated for 15 h in 7% potassium ferricyanide for iron (II) detection or in 7% ferrocyanide for iron (III) detection in aqueous hydrochloric acid (3%) and subsequently incubated in 0.75 mg/mL 3,3'-diaminobenzidine and 0.015% $H_2O_2$ for 5-10 min. The redox active iron is directly demonstrated by incubation of the tissue sections with 3% $H_2O_2$ and 0.75 mg/mL 3,3'-diaminobenzidine. The snap-frozen tissues are thawed and homogenized in 2 mL of PBS buffer (pH 7.4). The homogenate is digested in 500 μL concentrated $HNO_3$, followed by 500 μL $H_2O_2$ at 70° C., and further diluted in 1% $HNO_3$ for iron as well as Al, Cu, and Zn measurement by ICP-MS, which may performed by the Galbraith Laboratories, Inc. (Knoxville, Tenn.). All glassware in this study is prewashed by acidic solution and Milli-Q water to avoid iron and other metal contamination. For immunocytochemistry, sections are deparaffinized with xylene and rehydrated through graded ethanol. Endogenous peroxidase activity in the tissue is removed by a 30-min incubation with 3% $H_2O_2$ in methanol and nonspecific binding sites are blocked in a 30-min incubation with 10% normal goat serum in Tris-buffered saline (50 mM Tris-HCl and 150 mM NaCl, pH 7.6). Antibodies to markers of several well-described changes of Alzheimer's disease are used. These include rabbit antiserum to pentosidine, rabbit antiserum to HO-1, rabbit antiserum to tau, antisera to the lipid peroxidation adduct, hydroxynonenal (HNE) pyrrole [156], and a monoclonal antibody, 4G8 to amyloid-β. The immunostaining has been previously described by the peroxidase-antiperoxidase procedure using 3,3'-diaminobenzidine as cosubstrate. The sections are dehydrated through ethanol and xylene solutions and then mounted in Permount (Fisher). The specificity of each antibody will be confirmed by omitting the primary antibody or by performing adsorption experiments essentially as described previously.

Dose responses may be preformed to determine the optimum dosage. The cognitive ability of the Alzheimer transgenic mice treated by the chelator nanoparticle system are assayed using methods known in the art. The toxicity of both the metal free systems and their metal complexes are evaluated both in vitro and in vivo, and a kinetic analysis of uptake, distribution, and excretion may be performed.

Nanoparticles have been successfully linked to DFO and several other iron chelators and demonstrated to possess the ability to remove excess iron from AD subject's brain in vitro. These experiments showed that the conjugation did not affect the iron chelating capability, and instead, in some cases, improved the binding stability by converting three bi-dentate or two tri-dentate iron chelators into hexadentate chelators through nanoparticles as backbone linkages.

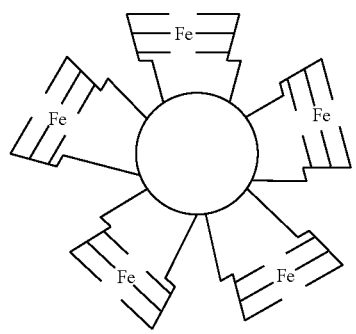

In vitro studies showed that some chelator-nanoparticle systems prefer to absorb specific LDL in human plasma, which help the LDL transports in the BBB recognize the chelator nanoparticle systems and transport them into the brain. To increase the ability of the system to be exported, the surface properties of the system was optimized by changing different chelators, linkages of conjugation, nanoparticles and other factors. It was found that some chelator-nanoparticle systems after binding metals indeed showed the increased absorption of certain Apolipoproteins, and thereby possessed the potential to re-cross the BBB of AD patient's brain through LDL transport mechanisms. Although these studies show the potential that the systems have the abilities to enter brain and bring excess metals out from the brain, in vivo studies may be performed to further confirm it.

Figure 10:
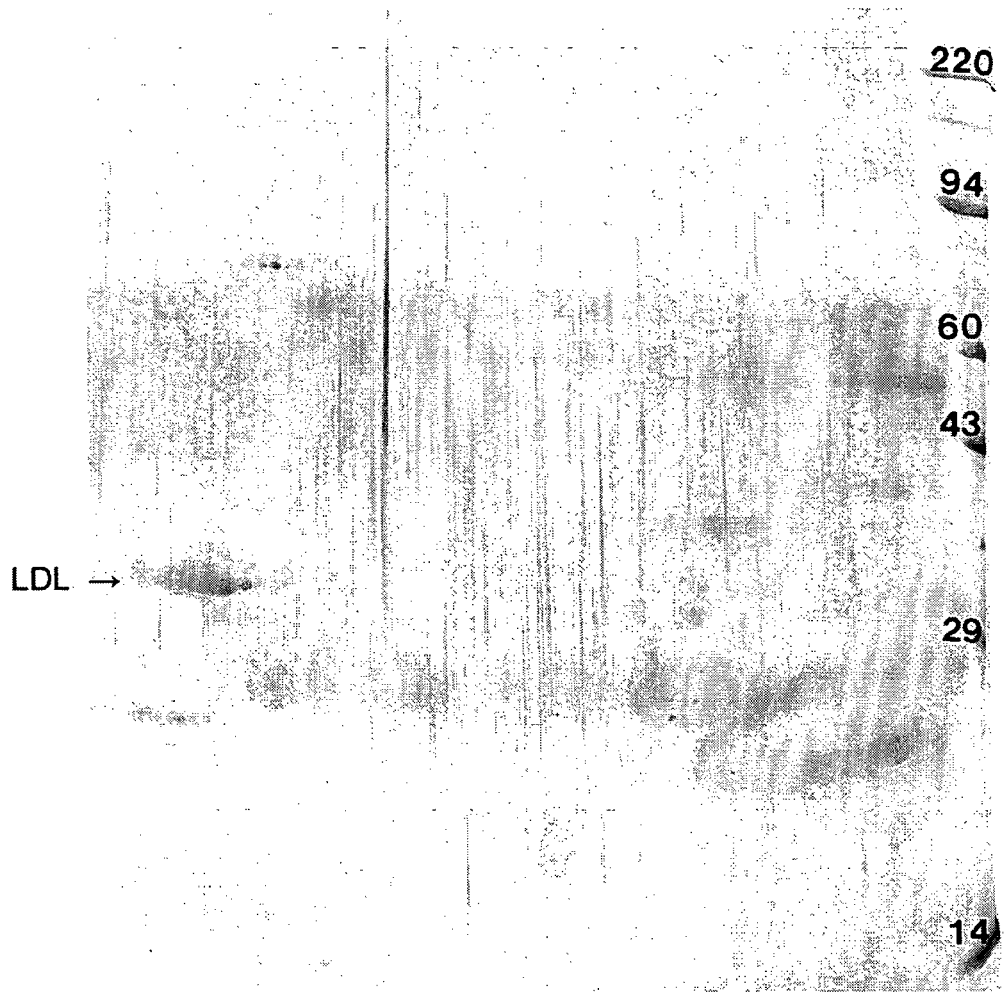
FIG. 10 shows a two-dimensional polyacrylamide gel electrophoresis (2-D PAGE) analysis of proteins absorbed by a chelator-nanoparticle system.

Two-dimensional polyacrylamide gel electrophoresis (2-D PAGE) analysis shows that the chelator-nanoparticle system may preferably absorb specific LDL (FIG. 10), which promotes the systems passage across the blood brain barrier, for example, by using a low density lipoprotein transport mechanism.

This approach may be applied to other iron related neurodegenerative disorders such as Parkinson's disease and Friedreich's ataxia. Because iron is also believed to play an important role in some chronic diseases such as heart disease, cancer and diabetic mellitus, as well as aging, using the chelator-nanoparticle systems to control the iron status is believed to be beneficial for these diseases as well.

All references, including publications, patents, and patent applications, cited herein are hereby incorporated by reference to the same extent as if each reference were individually and specifically indicated to be incorporated by reference and were set forth in its entirety herein.

REFERENCES

1. Halliwell B, Gutteridge J M C (1999) Free Radicals in Biology and Medicine. New York: Oxford Press.
2. Armstrong D. Free radicals in diagnostic medicine, Plenum, New York. 1994.
3. Knight J A (1999) Free Radicals, Antioxidants, Ageing and Disease. Washington, D.C.: AACC Press.
4. Symons M C R, Gutteridge J M C (1998) Free Radicals and Iron: Chemistry, Biology and Medicine. New York: Oxford University Press.
5. Kirk E A, Heinecke J W, LeBoeuf R C (2001) Iron overload diminishes atherosclerosis in apoE-deficient mice. J Clin Invest. 107:1545-53.
6. Writing Group for the Women's Health Initiative Investigators (2002) Risks and Benefits of Estrogen Plus Progestin in Healthy Postmenopausal Women: Principal Results From the Women's Health Initiative Randomized Controlled Trial. JAMA 288:321-333.
7. Lacey J V Jr, Mink P J, Lubin J H, Sherman M E, Troisi R, Hartge P, Schatzkin A, Schairer C (2002) Menopausal hormone replacement therapy and risk of ovarian cancer. JAMA 288:334-41.
8. Shlipak M G, Chaput L A, Vittinghoff E, Lin F, Bittner V, Knopp R H, Hulley S B; Heart and Estrogen/progestin Replacement Study Investigators (2003) Lipid changes on hormone therapy and coronary heart disease events in the Heart and Estrogen/progestin Replacement Study (HERS). Am Heart J 146:870-5.
9. Hulley S, Furberg C, Barrett-Connor E, Cauley J, Grady D, Haskell W, Knopp R, Lowery M, Satterfield S, Schrott H, Vittinghoff E, Hunninghake D; HERS Research Group (2002) Noncardiovascular disease outcomes during 6.8 years of hormone therapy: Heart and Estrogen/progestin Replacement Study follow-up (HERS II). JAMA 288:58-66.
10. Grady D, Herrington D, Bittner V, Blumenthal R, Davidson M, Hlatky M, Hsia J, Hulley S, Herd A, Khan S, Newby L K, Waters D, Vittinghoff E, Wenger N; HERS Research Group (2002) Cardiovascular disease outcomes during 6.8 years of hormone therapy: Heart and Estrogen/progestin Replacement Study follow-up (HERS II). JAMA. 288:49-57.
11. Wassertheil-Smoller S, Hendrix S L, Limacher M, Heiss G, Kooperberg C, Baird A, Kotchen T, Curb J D, Black H, Rossouw J E, Aragaki A, Safford M, Stein E, Laowattana S, Mysiw W J; WHI Investigators (2003) Effect of estrogen plus progestin on stroke in postmenopausal women: the Women's Health Initiative: a randomized trial. JAMA 289:2673-84.
12. Rapp S R, Espeland M A, Shumaker S A, Henderson V W, Brunner R L, Manson J E, Gass M L, Stefanick M L, Lane D S, Hays J, Johnson K C, Coker L H, Dailey M, Bowen D; WHIMS Investigators (2003) Effect of estrogen plus progestin on global cognitive function in postmenopausal women: the Women's Health Initiative Memory Study: a randomized controlled trial. JAMA 289:2663-72.
13. Shumaker S A, Legault C, Rapp S R, Thal L, Wallace R B, Ockene J K, Hendrix S L, Jones B N 3rd, Assaf A R, Jackson R D, Kotchen J M, Wassertheil-Smoller S, Wactawski-Wende J; WHIMS Investigators (2003) Estrogen plus progestin and the incidence of dementia and mild cognitive impairment in postmenopausal women: the Women's Health Initiative Memory Study: a randomized controlled trial. JAMA 289:2651-62.
14. Hartman D (1995) Free radical theory of aging: Alzheimer's disease pathogenesis. Age 18:97-119.
15. Kennard M L, Feldman H, Yamada T, Jefferies W A (1996) Serum levels of the iron binding protein p97 are elevated in Alzheimer's disease. Nat. Med 2:1230-5.
16. Halliwell B, Gutteridge J M C (1999) Free radicals in biology and medicine, Third edition, Oxford University press.
17. Kato I, Dnistrian A M, Schwartz M, Toniolo P, Koenig K, Shore R E, Zeleniuch-Jacquotte A (2000) Risk of iron overload among middle-aged women. Int J Vitam Nutr Res. 70:119-25.
18. Varanasi S S, Francis R M, Berger C E, Papiha S S, Datta H K (1999) Mitochondrial DNA deletion associated oxidative stress and severe male osteoporosis. Osteoporos Int 10:143-9.
19. Xu H, Watkins B A, Seifert M F (1995) Vitamin E stimulates trabecular bone formation and alters epiphyseal cartilage morphometry. Calcif Tissue Int. 57:293-300.
20. Chiba H, Uehara M, Wu J, Wang X, Masuyama R, Suzuki K, Kanazawa K, Ishimi Y (2003) Hesperidin, a citrus flavonoid, inhibits bone loss and decreases serum and hepatic lipids in ovariectomized mice. J Nutr. 133: 1892-7.
21. Recker R R, Saville P D, Heaney R P (1977) Effect of estrogens and calcium carbonate on bone loss in postmenopausal women. Ann Intern Med. 87:649-55.
22. Sen C K, Packer L (1996) Antioxidant and redox regulation of gene transcription. FASEB J 10:709-720.
23. Hogg N (1998) Free radicals in disease. Seminars Reproductive Endocrinology 16:241-8.
24. Berger C E, Horrocks B R, Datta H K (1998) CAMP-dependent inhibition is dominant in regulating superoxide production in the bone-resorbing osteoclasts. J Endocrinol 158:311-8.
25. Halliwell B, Gutteridge J M C (1984) Oxygen toxicity, oxygen radicals, transition metals and disease. Biochem J. 219:1-14.
26. Fenton H J H (1894) Oxidation of tartaric acid in presence of iron. J Chem Soc. 65:899-910.
27. Haber F, Weiss J (1934) The catalytic decomposition of hydrogen peroxide by iron salts. Proc. R. Soc. Lond. [A] 147:332-351.
28. Taylor D M, Williams D R (1995) Trace element medicine and chelation therapy. The Royal Society of Chemistry Paperbacks.
29. Boyer R F, Grabill T W, Petrovich R M (1988) Reductive release of ferritin iron: a kinetic assay. Anal Biochem. 174:17-22.
30. Puppo A, Halliwell B (1988) Formation of hydroxyl radicals from hydrogen peroxide in the presence of iron. Is haemoglobin a biological Fenton reagent? Biochem J. 249:185-90.
31. Lovell M A, Robertson J D, Teesdale W J, Campbell J L, Markesbery W R (1998) Copper, iron, and zinc in Alzheimer's disease senile plaques. J. Neurol. Sci. 158: 47-52.
32. Markesbery W R, Carney J M (1999) Oxidative alteration in Alzheimer's disease. Brain Pathology. 9:133-146.
33. Multhaup G, Schlicksupp A, Hesse L. et al. (1996) The amyloid precursor protein of Alzheimer's disease in the reduction of copper (II) to copper (I). Science 271:1406-9.

34. Sayre L M, Perry G, Smith M A (1999) Redox metals and neurodegenerative disease. Curr. Opin. Chem. Biol. 3:220-225.
35. Linder M C, Hazegh-Azam M (1996) Copper biochemistry and molecular biology. Am J Clin Nutr 63(suppl): 797S-811S.
36. Bush A I, Pettingell W H, Multhaup G, et al. (1994) Rapid induction of Alzheimer Aβ amyloid formation by zinc. Science 265:1464-7.
37. Hensley K, Carney J M, Mattson M P et al. (1994) A model for β-amyloid aggregation and neurotoxicity based on free radical generation by the peptide: relevance to Alzheimer's disease. Proc Natl Acad Sci USA 91:3270-4.
38. Butterfield D A (1997) β-amyloid-associated free radical oxidative stress and neurotoxicity; implications for Alzheimer's disease. Chem Res Toxicol 10:495-506.
39. Bruenger F W, Kuswik-Rabiega G, Miller S C. (1992) Decorporation of Aged americium deposits by oral administration of lipophilic polyamino carboxylic acids. J. Med. Chem. 35:112-118.
40. Miller S C, Bruenger F W, Kuswik-Rabiega G, Liu G, Lloyd R D (1993) Duration and dose-related effects of an orally administered, partially lipophilic polyaminocarboxylic acid on the decorporation of plutonium and americium. J Pharmacol Exp Ther. 267(1):548-54.
41. Liu G, Miller S C, Bruenger F W (1996) Efficient synthesis of N-[2-hydroxyethoxy)methyl]-2-alkyl-3-hydroxy-4-pyridinone by a modified Hilbert-Johnson reaction. Synthetic Communications 26:2681-2686.
42. Kalu N D (1991) The ovariectomized rat model of postmenopausal bone loss. Bone Mineral, 15:175-92.
43. Sonoda M, Yoshida I, Murase I (2001) Synthesis and determination of metal chelate stabilities of n-alkyltriethylenetetraaminepentaacetic acid. J Coord Chem 54:153-65.
44. Gassen M, Youdim M B H (1997) The potential role of iron chelators in the treatment of Parkinson's disease and related neurological disorders. Pharmacology & toxicology 80:159-166.
45. Liehr J G, Roy D (1998) "Pro-oxidant and antioxidant effects of estrogens" in Methods in molecular biology, vol. 108: Free radical and antioxidant protocols, Armstrong D Ed., Humana Press. 1998. p425-35.
46. Powell L W, George D K, McDonnell S M, Kowdley K V (1998) Diagnosis of hemochromatosis. Ann Intern Med. 129:925-31.
47. McLachlan D R, Dalton A J, Kruck T P, Bell M Y, Smith W L, Kalow W, Andrews D F (1991) Intramuscular desferrioxamine in patients with Alzheimer's disease. Lancet. 337:1304-8.
48. Cuajungco M P, Faget K Y, Huang X, Tanzi R E, Bush A I. (2000) Metal chelation as a potential therapy for Alzheimer's disease. Ann N Y Acad. Sci. 920:292-304.
49. Richardson D R, Ponka P (1998) The development of iron chelators to treat iron overload disease and their use as experimental tool to study intracellular iron metabolism. Am J Hematol. 58:299-305.
50. Keberle H (1964) The biochemistry of desferrioxamine and its relation to iron metabolism. Ann NYA Sci. 119: 758-768.
51. Hider R C, Hall A D (1991) Clinically useful chelators of tripositive elements. Prog Med. Chem. 28:41-173.
52. Loske C, Gerdemann A, Schepl W, Wycislo M, Schinzel R, Palm D, Riederer P, Muench G (2000) Transition metal-mediated glycoxidation accelerates cross-linking of β-amyloid peptide. Eur. J. Biochem. 267:4171-78.
53. Cherny R A, Legg J T, Mclean C A, Fairlie D P, Huang X, Atwood C S, Beyreuther K, Tanzi R E, Masters C L, Bush A I (1999) Aqueous dissolution of Alzheimer's disease Aβ amyloid deposits by biometal depletion. J Biol Chem 274:23223-8.
54. Crowe A, Morgan E H (1994) Effects of chelators on iron uptake and release by the brain in the rat. Neurochem Res. 19:71-6.
55. Kontoghiorghes G J (1995) New concepts of iron and aluminum chelation therapy with oral L1 (deferiprone) and other chelators. Analyst 120:845-51.
56. Floor E (2000) Iron as a vulnerability factor in nigrostriatal degeneration in aging and Parkinson's disease. Cell Mol. Biol. 46:709-20.
57. Struck M, Waldmeier P, Berdoukas V. The treatment of iron overload-psychiatric implication. In: Iron in central nervous system disorders, Riederer P, Youdim MBH eds. Springer Verlag, Wien, 1993, pp 189-196.
58. Mueller R H, Heinemann S (1989) Microparticles as parenteral systems with high tissue affinity, in: R Gurny, H E Junginer (Eds.) Bioadhesion. Possibilities and future trends, Wissenshaftliche, Stuttgart, pps. 202-214.
59. Luck M, Schroder W, Harnisch S, Thode K, Blunk T, Paulke B R, Kresse M, Muller R H (1997) Identification of plasma proteins facilitated by enrichment on particulate surfaces: analysis by two-dimensional electrophoresis and N-terminal microsequencing. Electrophoresis.18:2961-7.
60. Smith M A, Hirai K, Hsiao K, Pappolla M A, Harris P L, Siedlak S L, Tabaton M, Perry G (1998) Amyloid-beta deposition in Alzheimer transgenic mice is associated with oxidative stress. J. Neurochem. 70:2212-5.
61. Kreuter J (2001) Nanoparticulate systems for brain delivery of drugs. Adv Drug Deliv Rev. 47:65-81.
62. Muller R H, Jacobs C, Kayser O (2001) Nanosuspensions as particulate drug formulations in therapy. Rationale for development and what we can expect for the future. Adv Drug Deliv Rev. 47:3-19.
63. Ebina Y, Okada S, Hamazaki S, Toda Y, Midorikawa O (1991) Impairment of bone formation with aluminum and ferric nitrilotriacetate complexes. Calcif Tissue Int. 48:28-36.
64. Porter J B, Morgan J, Hoyes K P, Burke L C, Huehns E R, Hider R C (1990) Relative oral efficacy and acute toxicity of hydroxypyridin-4-one iron chelators in mice. Blood. 76:2389-96.
65. Hider R C, Choudhury R, Rai B L, Dehkordi L S, Singh S (1996) Design of Orally active iron chelators. Acta Haematol 95:6-12.
66. Martell A E, Motekaitis R J, Sun Y, Ma R. Welch M J, Pajeau T (1999) New chelating-agents suitable for the treatment of iron overload. Inoganica Chimica Acta. 291: 238-246.
67. Caravan P, Orvig C (1997) Tripodal aminophenolate ligand complexes of aluminum(III), gallium(III), and indium(III) in water. Inorg. Chem. 36:236-248.
68. Faller B, Spanka C, Sergejew T, Tschinke V (2000) Improving the oral bioavailability of the iron chelator HBED by breaking the symmetry of the intramolecular H-bond network. J. Med. Chem. 43:1467-75.
69. Raymond K N, Xu J (1994) Siderophore-based hydroxypyridonate sequestering agents, in The development of iron chelators for clinical use. Bergeron R J, Brittenham G M, Eds, CRC Boca Raton. pp 354-371.
70. Bergeron R J, McManis J S (1994) Sythesis and biological activity of hydroxamate-based iron chelators, in The development of iron chelators for clinical use. Bergeron R J, Brittenham G M, Eds, CRC Boca Raton. pp 237-273.

71. Porter J B, Gyparaki M, Burke L C, Huehns E R, Sarpong P, Saez V, Hider R C (1988) Iron metabolisation from hepatocyte monolayer cultures by chelators: the importance of membrane permeability and the iron binding constant. Blood. 72:1497-1503.

72. Muhlbauer R C, Li F. Effect of vegetables on bone metabolism. Nature. 1999 Sep. 23;401(6751):343-4.

73. Kreijkamp-Kaspers S, Kok L, Grobbee D E, de Haan E H, Aleman A, Lampe J W, van der Schouw Y T. Effect of soy protein containing isoflavones on cognitive function, bone mineral density, and plasma lipids in postmenopausal women: a randomized controlled trial. JAMA. 2004 Jul. 7;292(1):65-74.

74. Kenner G H, Brik A B, Liu G, Haskell E H, Hayes R B, Knight J A, Vajda E G, Miller S C, Jee W S S, Barrus J K, Variation of long-lived free radicals responsible for EPR native signal in bone of aged or diseased human females and ovariectomized adult rats. Radiation Measurements (in press).

75. Haskell E H, Hayes R B, Kenner G H, Wieser A, Aragno D, Fattibene P, Onori S (1999) Achievable resolution and accuracy in EPR dosimetry of tooth enamel. Rad. Prot. Dosim. 84:527-535.

76. Waynforth H B (1980) Experimental and Surgical Techniques in the Rat. Academic Press, London.

77. May P M, Bulman R A (1983) The present status of chelating agents in medicine. Prog Med. Chem. 20:225-336.

78. Klaasen C D. Heavy metals and heavy-metalantagonists. In: Goodman and Gilman's The pharmacological basis of therapeutics, 9th ed., Hardman J G, Limbird L E, Molinoff P B, Ruddon R W, Gilman A G eds. McGraw Hill, New York, 1996, pp 1649-71.

79. Blake D R, Winyard P, Lunec J, Williams A, Good P A, Crewes S J, Gutteridge J M, Rowley D, Halliwell B, Cornish A, Hider R C (1985) Cerebral and ocular toxicity induced by desferrioxamine. Q J. Med. 56:345-55.

80. Kruck T P, Fisher E A, McLachlan D R (1993) A predictor for side effects in patients with Alzheimer's disease treated with deferoxamine mesylate. Clin Pharmacol Ther. 53:30-7.

81. Miller S C, Jee WSS (1975) Ethane-1-hydroxy-1,1-diphosphonate (EHDP) effects on growth and modeling of the rat tibia. Calcif Tissue Res 18:315-21.

82. Liu G, Miller S C, Bruenger F W (1996) Efficient synthesis of N-[2-hydroxyethoxy)methyl]-2-alkyl-3-hydroxy-4-pyridinone by a modified Hilbert-Johnson reaction. Synthetic Communications 26:2681-2686.

83. Dobbin P S, Hider R C, Hall A D, Taylor P D, Sarpong P, Porter J B, Xiao G, van der Helm D (1993) Synthesis, physicochemical properties, and biological evaluation of N-substituted 2-alkyl-3-hydroxy-4(1H)-pyridinones: orally active iron chelators with clinical potential. J Med. Chem. 36(17):2448-58.

84. Hsiao K, Chapman P, Nilsen S, Eckman C, Harigaya Y, Younkin S, Yang F, Cole G (1996) Correlative memory deficits, Abeta elevation, and amyloid plaques in transgenic mice. Science. 274:99-102.

85. Smith M A, Hirai K, Hsiao K, Pappolla M A, Harris P L, Siedlak S L, Tabaton M, Perry G (1998) Amyloid-beta deposition in Alzheimer transgenic mice is associated with oxidative stress. J. Neurochem. 70:2212-5.

86. Liu G, Bruenger F W, Barrios A M, Miller S C (1995) Synthesis of 2-alkyl-3-hydroxy-4-pyridinone-ribonucleosides. Potential oral iron chelators. Nucleosides Nucleotides 14:1091-1904.

87. Miller S C, Bowman B M, Miller M A, Bagi C M (1991) Calcium adsorption and osseous organ-, tissue-, and envelope-specific changes following ovariectomy in rats. Bone 12:439-446.

88. Miller M A, T H Omura, S C Miller. Increased cancellous bone remodeling during lactation in beagles. Bone 10:279-285, 1989.

89. Wong S S. Chemistry of protein conjugation and cross-linking. CRC: Boca Raton; 1993.

90. Arano Y, Matsushima H, Tagawa M, Koizumi M, Endo K, Konishi J, Yokoyama A. A novel bifunctional metabolizable linker for the conjugation of antibodies with radionuclides. Bioconjug Chem 2:71-76, 1991.

91. Dobbin P S, Hider R C, Hall A D, Taylor P D, Sarpong P, Porter J B, Xiao G, Van der Helm D. Synthesis, physicochemical properties, and biological evaluation of N-substituted 2-alkyl-3-hydroxy-4(1H)-pyridinones: orally active iron chelators with clinical potntial. J Med Chem 36:2448-58, 1993.

92. Mathias C J, Sun Y Z, Welch M J, Connett J M, Philpott G W, Martell A E (1990) N,N'-bis(2-hydroxybenzyl)-1-(4-bromoacetamidobenzyl)-1,2-ethylenediamine-N,N'-diacetic acid: a new bifunctional chelate for radiolabeling antibodies. Bioconjug Chem. 1:204-11.

What is claimed is:

1. A method of treating bone loss, said method comprising administering an effective amount of an alkyltriethylenetetraminepentaacetic acid having a structure represented by a formula:

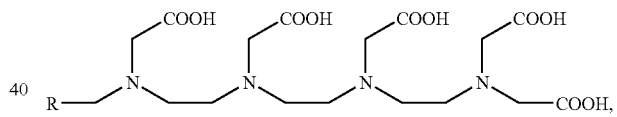

wherein R is long chain alkyl, to a subject diagnosed with a bone-loss disease associated with increased iron concentrations, thereby treating bone loss in the subject.

2. The method according to claim 1, wherein the alkyltriethylenetetraminepentaacetic acid is 1-N-docosyltriethylenetetraminepentaacetic acid.

3. The method according to claim 1, wherein the disease associated with increased iron concentrations is osteoporosis.

4. The method according to claim 1, further comprising administering an effective amount of vitamin E to the subject.

5. The method according to claim 1, wherein the alkyltriethylenetetraminepentaacetic acid is conjugated to a nanoparticle, thereby producing a alkyltriethylenetetraminepentaacetic acid nanoparticle conjugate.

6. The method according to claim 1, further comprising increasing trabecular bone volume in the subject.

7. The method according to claim 1, further comprising decreasing marrow space in the bone of the subject.

8. The method according to claim 1, wherein the disease associated with increased iron concentrations is osteopenia.

9. A method of treating bone loss, said method comprising administering an effective amount of an alkyltriethylenetetraminepentaacetic acid having a structure represented by a formula:

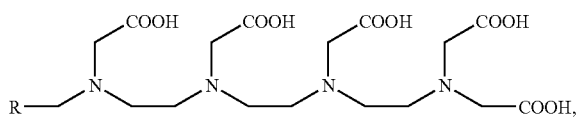

wherein R is long chain alkyl, to a subject diagnosed with osteoporosis, thereby treating bone loss in the subject.

10. The method according to claim 9, wherein the alkyltriethylenetetraminepentaacetic acid is 1-N-docosyltriethylenetetraminepentaacetic acid.

11. The method according to claim 9, further comprising administering an effective amount of vitamin E to the subject.

12. The method according to claim 9, wherein the alkyltriethylenetetraminepentaacetic acid is conjugated to a nanoparticle, thereby producing a alkyltriethylenetetraminepentaacetic acid nanoparticle conjugate.

13. The method according to claim 9, further comprising increasing trabecular bone volume in the subject.

14. The method according to claim 9, further comprising decreasing marrow space in the bone of the subject.

* * * * *

UNITED STATES PATENT AND TRADEMARK OFFICE
CERTIFICATE OF CORRECTION

| | | |
|---|---|---|
| PATENT NO. | : 7,728,038 B2 | Page 1 of 1 |
| APPLICATION NO. | : 11/197959 | |
| DATED | : June 1, 2010 | |
| INVENTOR(S) | : Gang Liu and Ping Men | |

It is certified that error appears in the above-identified patent and that said Letters Patent is hereby corrected as shown below:

IN THE SPECIFICATION

In column 1, lines 13-17, replace "This invention was made with government support under Grants 1R21 NS044064-01A1 and 1R03AG21300-01 awarded by the National Institute of Neurological Disorders and Stroke, and the National Institute on Aging. The United States Government has certain rights in the invention." with -- This invention was made with government support under R21 NS044064 and R01 AG021300 awarded by National Institutes of Health. The government has certain rights in the invention. --

Signed and Sealed this
Eleventh Day of August, 2015

Michelle K. Lee
*Director of the United States Patent and Trademark Office*

UNITED STATES PATENT AND TRADEMARK OFFICE
CERTIFICATE OF CORRECTION

PATENT NO. : 7,728,038 B2  
APPLICATION NO. : 11/197959  
DATED : June 1, 2010  
INVENTOR(S) : Gang Liu and Ping Men Page 1 of 1

It is certified that error appears in the above-identified patent and that said Letters Patent is hereby corrected as shown below:

IN THE SPECIFICATION

In column 1, lines 14-17, replace "Grants 1R21 NS044064-01A1 and 1R03AG21300-01 awarded by the National Institute of Neurological Disorders and Stroke, and the National Institute on Aging. The United States Government has certain rights in the invention." with -- R21 NS044064 and R01 AG021300 awarded by National institutes of Health. The government has certain rights in the invention. --

Signed and Sealed this
Twentieth Day of October, 2015

Michelle K. Lee
*Director of the United States Patent and Trademark Office*

UNITED STATES PATENT AND TRADEMARK OFFICE
CERTIFICATE OF CORRECTION

PATENT NO. : 7,728,038 B2
APPLICATION NO. : 11/197959
DATED : June 1, 2010
INVENTOR(S) : Liu et al.

It is certified that error appears in the above-identified patent and that said Letters Patent is hereby corrected as shown below:

This certificate supersedes the Certificate of Correction issued on October 20, 2015. The certificate which issued on October 20, 2015 is vacated since the request for the Certificate of Correction to correct the government rights statement was already issued. The Certificate of Correction which issued on October 20, 2015 was published in error and should not have been issued for this patent.

Signed and Sealed this
Eighth Day of December, 2015

Michelle K. Lee
*Director of the United States Patent and Trademark Office*